United States Patent
Imler et al.

(10) Patent No.: US 11,091,810 B2
(45) Date of Patent: Aug. 17, 2021

(54) FOCAL GENE EXPRESSION PROFILING OF STAINED FFPE TISSUES WITH SPATIAL CORRELATION TO MORPHOLOGY

(71) Applicants: Elliot Imler, Tuscon, AZ (US); Milos Babic, Vista, CA (US); Bruce Seligmann, Tuscon, AZ (US); BioSpyder Technologies, Inc., Carlsbad, CA (US)

(72) Inventors: Elliot Imler, Tucson, AZ (US); Milos Babic, Vista, CA (US); Bruce Seligmann, Tucson, AZ (US)

(73) Assignee: BioSpyder Technologies, Inc., Carlsbad, CA (US)

( * ) Notice: Subject to any disclaimer, the term of this patent is extended or adjusted under 35 U.S.C. 154(b) by 0 days.

(21) Appl. No.: 15/954,546

(22) Filed: Apr. 16, 2018

(65) Prior Publication Data

US 2018/0237864 A1    Aug. 23, 2018

Related U.S. Application Data

(63) Continuation-in-part of application No. PCT/US2018/024206, filed on Mar. 23, 2018, and a continuation-in-part of application No. 15/387,650, filed on Dec. 22, 2016, which is a continuation-in-part of application No. PCT/US2016/014999, filed on Jan. 26, 2016, which is a continuation-in-part of application No. 14/788,670, filed on Jun. 30, 2015, now Pat. No. 9,856,521, said application No. 15/387,650 is a continuation-in-part of application No. 14/788,670, filed on Jun. 30, 2015, now Pat. No. 9,856,521.

(60) Provisional application No. 62/108,161, filed on Jan. 27, 2015, provisional application No. 62/475,796, filed on Mar. 23, 2017.

(51) Int. Cl.
| | |
|---|---|
| C12Q 1/68 | (2018.01) |
| C07H 21/00 | (2006.01) |
| C12Q 1/6886 | (2018.01) |
| C12Q 1/6806 | (2018.01) |

(52) U.S. Cl.
CPC ......... *C12Q 1/6886* (2013.01); *C12Q 1/6806* (2013.01); *C12Q 2600/112* (2013.01); *C12Q 2600/156* (2013.01)

(58) Field of Classification Search
CPC .. C12Q 1/68; C12Q 2526/00; C12Q 2600/00; C07H 21/00
See application file for complete search history.

(56) References Cited

U.S. PATENT DOCUMENTS

| | | | | |
|---|---|---|---|---|
| 4,988,617 A * | 1/1991 | Landegren | ........... | C12Q 1/6827 435/6.11 |
| 5,843,644 A * | 12/1998 | Liotta | ................. | G01N 1/2813 435/6.12 |
| 8,265,362 B2 * | 9/2012 | Sano | ................... | A61B 5/0059 382/128 |
| 9,856,521 B2 * | 1/2018 | Stevens | ............... | C12Q 1/6827 |
| 9,938,566 B2 * | 4/2018 | Shepard | ............... | C12Q 1/6813 |
| 9,957,550 B2 * | 5/2018 | Yeakley | ............... | C12Q 1/6816 |
| 2003/0104434 A1 * | 6/2003 | Fan | ...................... | C12Q 1/6816 435/6.12 |
| 2005/0009821 A1 * | 1/2005 | Pyring | ................. | C07D 417/06 514/235.5 |
| 2006/0275782 A1 * | 12/2006 | Gunderson | .......... | C12Q 1/6874 435/6.12 |
| 2009/0156536 A1 * | 6/2009 | Kim | ...................... | C07K 16/30 514/44 R |
| 2010/0256017 A1 * | 10/2010 | Larman | ................ | B01J 19/0046 506/40 |
| 2010/0267571 A1 * | 10/2010 | Watanabe | ............ | C12Q 1/6806 506/7 |
| 2011/0045462 A1 * | 2/2011 | Fu | ........................ | C12Q 1/6809 435/6.13 |
| 2012/0164638 A1 * | 6/2012 | Vogelstein | ........... | C12Q 1/6816 435/6.11 |
| 2012/0196768 A1 * | 8/2012 | Kuroda | ............... | C12N 15/1003 506/9 |
| 2013/0260384 A1 * | 10/2013 | Goldkorn | ............. | C12Q 1/6886 435/6.12 |
| 2014/0363843 A1 * | 12/2014 | Laugharn, Jr. | ........ | G01N 1/2813 435/40.5 |
| 2015/0307947 A1 * | 10/2015 | Basu | ..................... | C12Q 1/6886 506/2 |
| 2017/0191937 A1 * | 7/2017 | Levenson | .......... | G01N 21/6458 |
| 2018/0163265 A1 * | 6/2018 | Zhang | .................. | C12Q 1/6855 |
| 2018/0208967 A1 * | 7/2018 | Larman | ................ | C12Q 1/6806 |

OTHER PUBLICATIONS

The Stratagene Catalog , p. 39 (Year: 1988).*
Urieli-Shoval et al., J. of Histochemistry and Cytochemistry 40(12) :1879 (Year: 1992).*
Ahern H., The Scientist 9(15) :20 (Year: 1995).*
Emmert-Buck et al., Science 274 : 998 (Year: 1996).*
Bonner et al. Science 278 :1481 (Year: 1997).*
Fend et al., Am J. of Pathology 154 (1) :61 (Year: 1999).*
Huang et al., PNAS 98(26) : 15044 (Year: 2001).*
Lehmann et al. Methods 25 : 409 (Year: 2001).*
Bibikova et al., Quantitative Gene Expression Profiling in FormalinFixed, Paraffin-Embedded Tissues Using Universal Bead Arrays. Am. J. of Pathology 165 (5) :1799 (Year: 2004).*

(Continued)

*Primary Examiner* — Ethan C Whisenant

(57) ABSTRACT

Expression profiling of FFPE sample areas smaller than 2 mm² with single-cell sensitivity, correlated with tissue microenvironment morphology and neoplastic grade. An automated digital molecular pathology instrument for integrated imaging, immunohistochemical assessment, and processing samples for sequence detection assays. Software for instrument and sample control and analysis.

26 Claims, 9 Drawing Sheets

(56) References Cited

OTHER PUBLICATIONS

Hunt et al., Arch Pathol Lab Med 128 :1372 (Year: 2004).*
Tangrea et al., Diagn Mol Pathol 13(13(4) :207 (Year: 2004).*
Espina et al., Nature Protocols 1(2) : 586 (Year: 2006).*
Roy et al., Physiol Genomics 25 :364 (Year: 2006).*
Abramovitz et al., Biotechniques 44(3) : 417 (Year: 2008).*
Da Silva et al., AM J. of Surgical Pathology 32 (5) 773 (Year: 2008).*
Farragher et al. Histochem Cell Biol. 130 :435 (Year: 2008).*
Soderberg et al., Methods 45 : 227 (Year: 2008).*
Larsson et al., Nature Methods 7(5) : 395 (Year: 2010).*
Weibrecht et al. Nature Protocols 8(2) :355 (Year: 2013).*
Larman et al., Nucleic Acids Research 42(14) : 9146 (Year: 2014).*
Credle et al. Nucleic Acids Research 45(14 :e128 (Year: 2017).*

* cited by examiner

*Fig. 2*
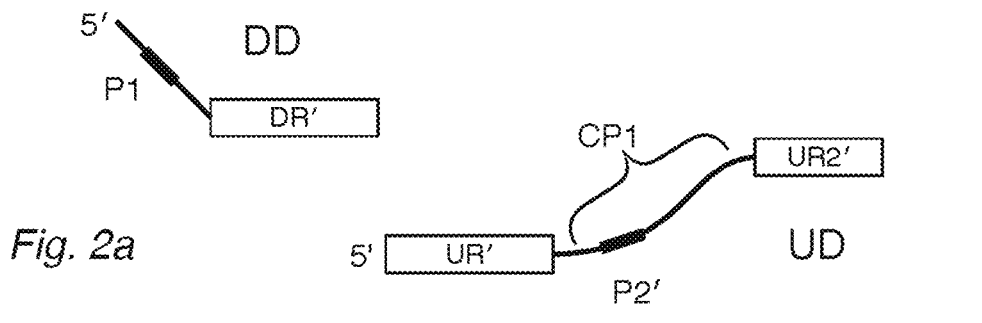
*Fig. 2a*
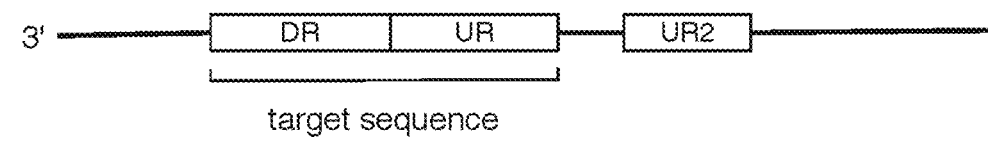
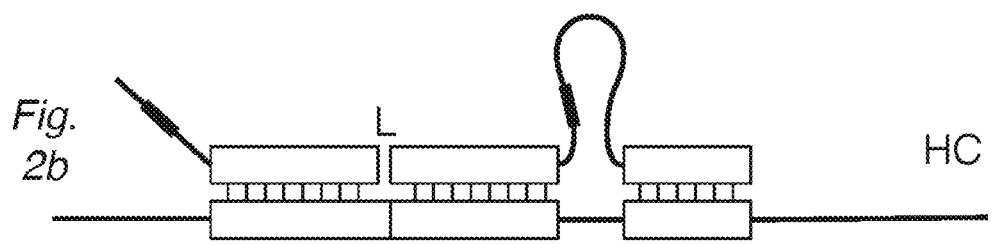
*Fig. 2b*
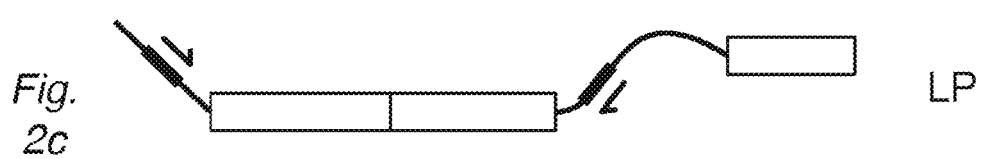
*Fig. 2c*
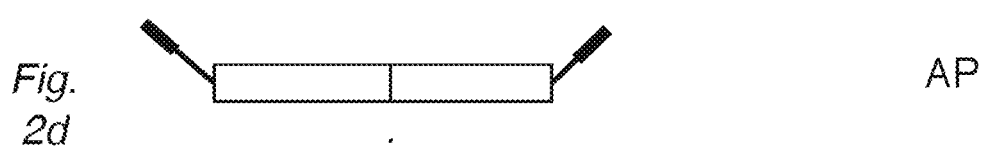
*Fig. 2d*

H&E stained, processed in situ

Post-Elution

Pre-Elution

CellSensus profiling of 130 µm diameter areas

Post-Elution

Pre-Elution

FOCAL GENE EXPRESSION PROFILING OF STAINED FFPE TISSUES WITH SPATIAL CORRELATION TO MORPHOLOGY

CROSS-REFERENCE TO RELATED APPLICATIONS

This application is a continuation-in-part of Ser. No. 15/387,650 entitled Ligation Assays in Liquid Phase, filed Dec. 22, 2016 and published as US 2017/0101671, which is a continuation-in-part of international application PCT/US16/14999, filed Jan. 26, 2016 and published as WO 2016/123154, which is a continuation-in-part of Ser. No. 14/788,670, filed Jun. 30, 2015 and issued as U.S. Pat. No. 9,856,521 on Jan. 2, 2018, which claims the benefit of priority of U.S. provisional application Ser. No. 62/108,161, filed Jan. 27, 2015.

Parent application Ser. No. 15/387,650, is also a continuation-in-part of Ser. No. 14/788,670, filed Jun. 30, 2015 and issued as U.S. Pat. No. 9,856,521 on Jan. 2, 2018, which claims the benefit of priority of U.S. provisional application Ser. No. 62/108,161, filed Jan. 27, 2015.

This application is also a continuation-in-part of international application PCT/US18/24206, entitled Modulation of Targets in Cellular Pathways Identified by Resolution of Stochastic Gene Expression, filed Mar. 23, 2018, which claims the benefit of priority of U.S. provisional application Ser. No. 62/475,796, filed Mar. 23, 2017.

The contents of the aforementioned applications are incorporated herein in their entirety.

STATEMENT OF GOVERNMENT SUPPORT

This invention was made with government support under grants R43 & R44 ES024107, R43 & R44 HG007339, R43 & R44 HG008917, R43 & R44 HG007815, R33CA183699, awarded by the National Institutes of Health (NIH). The government has certain rights in the invention.

TECHNICAL FIELD

This invention relates to histology, and more particularly to assays for detecting nucleic acid sequences in tissue samples.

SUMMARY OF THE INVENTION

The present invention provides methods, kits, instruments, and software for profiling nucleic acid sequences in minute focal areas of histological samples, such as formalin-fixed, paraffin-embedded tissue specimens (FFPEs).

The detection assays disclosed herein (in different versions, but collectively TempO-Seq™ assays) enable gene expression to be profiled from areas 1 mm$^2$ and smaller focal areas of, for example, of 5 µm thick FFPE sections of normal and cancerous tissue to identify disease biomarkers and mechanistic pathways. The invention can also be performed in situ on slides by an automated slide stainer, followed by antibody staining and/or H&E (hematoxylin and eosin) staining. Then, using a digital imaging platform such as the automated CellSensus™ digital imaging platform of the invention, areas as small as 130 µm down to 30 µm in diameter within the FFPE section can be profiled, permitting the gene expression data to be correlated directly to the specific morphology of that focal area. Smaller and irregular areas of FFPE can also be profiled. Any preparation on slides can be profiled, such as cells fixed to a surface, and the number of cells or amount of tissue can be as little as a single cell or portion of a cell, such as a portion of a neuron.

Pathologists can use the instrument and software of the invention to select areas to be profiled for marker expression during the course of their histologic examination of the section. Detection assay products (such as ligated detector oligonucleotides) can be recovered automatically by the instrument from the selected regions of interest. After transferring the products into PCR tubes, any remaining steps in the detection assay can be completed, such as PCR amplification or preparation for sequencing. Analysis of the sequencing data can be carried out automatically by the software to report results. In the present invention, laser capture and destruction of the tissue become unnecessary. The slides processed by the invention can be dried, treated to stabilize or preserve the sample, or otherwise archived, and additional areas can be sampled at a later date.

Replicate areas of matched normal versus cancerous tissue can be sampled, measuring gene biomarkers of clinical utility. Gene expression profiles are presented for scraped areas of normal, high grade PIN (prostatic intraepithelial neoplasia), and cancer epithelium from prostate cancer patients to perform the TempO-Seq™ assay on H&E-stained FFPE samples. The single-cell sensitivity of the in situ protocol is demonstrated by comparing profiles of single MCF-7 cells from a processed Cytospin slide to single cells collected by flow cytometry. The reproducibility of the assay is demonstrated for H&E-stained FFPE samples, as well as the specificity of biomarker expression obtained from profiling areas of stroma, normal and cancer epithelium. These data demonstrate that the automated CellSensus™ platform and assays enable complex molecular tests to be carried out by pathologists in their own labs, and render moot the issues of "% cancer" and the amount of patient tissue required for testing. They demonstrate that spatial resolution and specificity result in greater biomarker specificity. The present invention brings extraction-free complex molecular testing of FFPEs into the pathology lab and provides simplicity, focal spatial precision and correlation to morphology to the field of molecular pathology. While the results presented use fixed tissue or cells on a slide, any surface-adherent sample can be tested as long as it survives the wash steps and the intracellular nucleic acid to be measured is accessible to the reagents.

H&E- or antibody-stained FFPEs can be assayed, providing whole-transcriptome or focused panels of data using as little as 1 mm$^2$ area of a 5 mm section. Molecular profiling of high grade PIN adjacent to cancer versus cancer is consistent with adjacent high grade PIN being cancer in situ. Slides can be processed though the in situ assay using an automated stainer, and antibody or H&E staining can be performed on the processed slides. Immunohistochemistry (IHC) assessment can be carried out and areas for automated profiling selected using the CellSensus™ digital molecular pathology platform. The sample can be any surface-adherent sample, such as FFPE or cells. The in situ assay has single-cell sensitivity, even for measuring low-expressed genes. The area profiled is marked so that profiling data can be positively correlated to the tissue microenvironment morphology. Accordingly, the spatial resolution results in biomarker specificity.

Accordingly, the present invention provides a method for detecting a nucleic acid sequence from a selected area of a sample in situ, comprising in any order: imaging the sample for the presence or absence of an analyte; selecting an area of the sample less than 2 mm$^2$ based on the imaging; detecting a target nucleic acid sequence having a downstream region (DR) and an upstream region (UR). The detection step is performed by contacting at least the selected area of the sample with a downstream detector oligo (DDO) comprising a DR' portion that is complementary to the DR, and an upstream detector oligo (UDO) comprising a UR' portion that is complementary to the UR, ligating the DR' and UR' if both are specifically hybridized to the DR and UR of a target sequence, and collecting the ligation products from the selected area. As a result, the ligation product indicates the presence of the target sequence in the selected area.

The invention also provides a method for detecting a neoplastic state of a cell by performing the method of the invention where a first cancer marker sequence is detected in the cell. The invention also provides a method for generating a gene expression profile for the selected area, for a plurality of target sequences. A disease state can be diagnosed by performing the method, wherein the target sequence is detected in the area of a morphological feature. The invention also provides kits of detector oligos and stains. The invention further provides an instrument having an imaging component, a component for collecting ligation products from the selected area, and a component for transferring the products to an external container.

BRIEF DESCRIPTION OF THE DRAWINGS

FIG. 2a shows an "anchored" version of the assay where the UD is configured with a second complementary region (UR2' or "anchor") separated by a noncomplementary region (CP1). The DD and UD can hybridize to a target sequence as in FIG. 2b, forming a hybridization complex (HC) providing a substrate for ligation at the junction (L) between DR' and UR'. In some methods, an optional nuclease, such as a 3'- or 5'-single-stranded exonuclease, is provided at various stages to remove undesired or leftover reactants. After ligation, FIG. 2c shows the ligation product (LP) can be amplified by primers to yield amplification products (AP) in FIG. 2d.

DETAILED DESCRIPTION OF THE INVENTION

Ligation Assays, Generally

Figure 1:
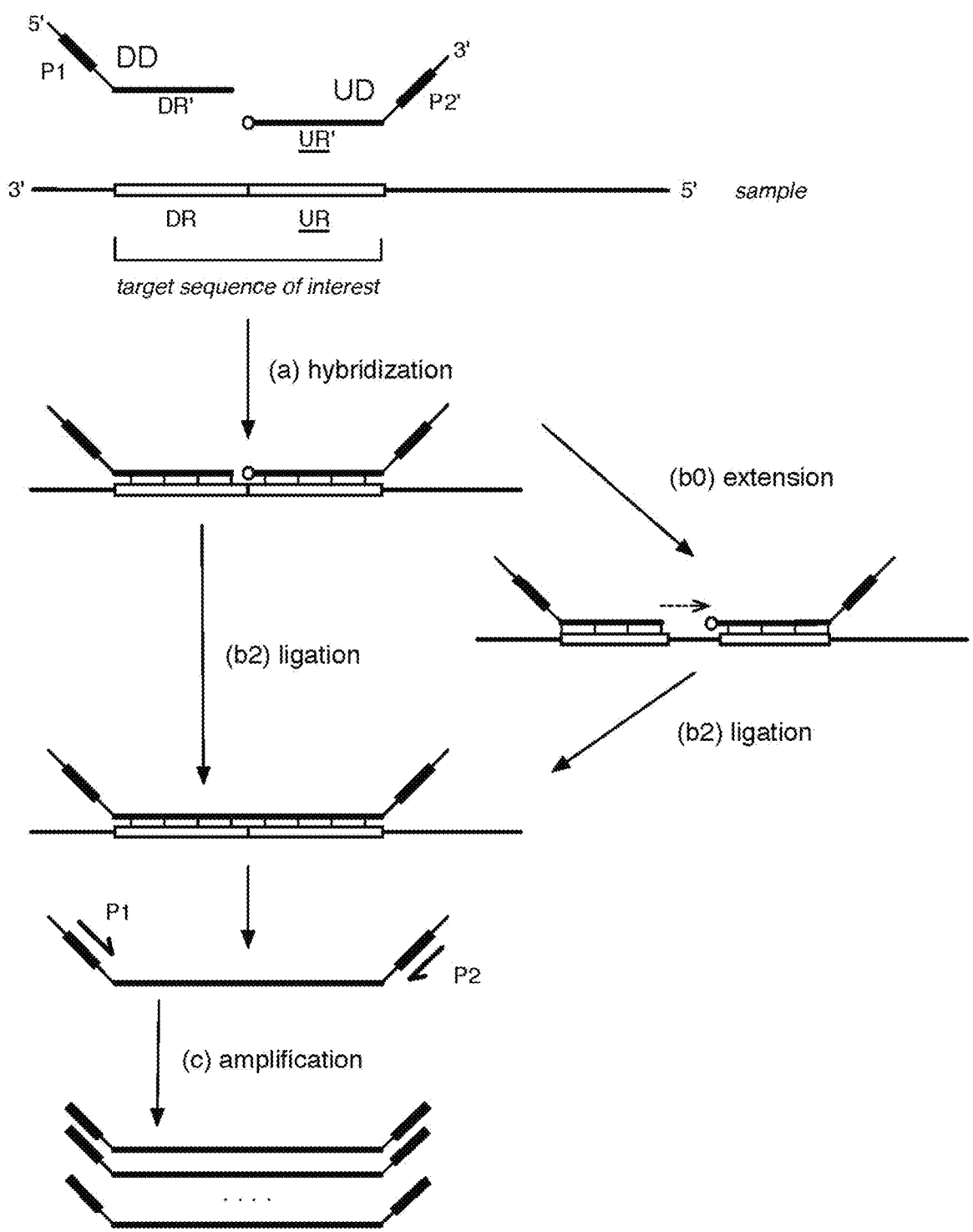
FIG. 1 illustrates a representative ligation assay for detecting target nucleic acid sequences. Briefly, downstream detector (DD) and upstream detector (UD) probe oligonucleotides are allowed to (a) hybridize to a target sequence, having DR and UR regions, in a sample. For convenience of identification, upstream regions are often underlined herein. While hybridized to the DR and UR of the target sequence, the DD is (b2) ligated selectively to the UR. Optionally, the DD is (b0) extended prior to (b2) ligation. The ligation product is optionally (c) amplified via amplification regions P1 and P2' by one or more primers, such as P1 and P2.

A typical ligation assay is illustrated schematically in FIG. 1, which is discussed in more detail in Example 1. A sample that may contain target sequences is contacted with a pool of detector oligonucleotide probes ("probes" or "detectors"). For each target sequence, a pair of detectors is provided: a downstream detector (DD) and an upstream detector (UD). A downstream detector can have a portion (DR') that is complementary to a region of the target sequence designated as a downstream region (DR). An upstream detector can have a portion (UR') that is complementary to a region of the target sequence designated as the upstream region (UR). Here, the terms "downstream" and "upstream" are used relative to the 5'-to-3' direction of transcription when the target sequence is a portion of an mRNA, and for convenience the regions designated as upstream are often shown underlined.

As shown in FIG. 1, the DR' of the DD and the UR' of the UD for each target sequence are allowed to hybridize to the corresponding DR and UR of the target sequence, if present in the sample. When the DR and UR of a target sequence are adjacent and the DR' and UR' of the pair of detector oligos are specifically hybridized to the target sequence to form a hybridization complex, the adjacent detectors DD and UD can be ligated. Thus, formation of a DD—UD ligation product serves as evidence that the target sequence (DR—UR) was present in the sample. In cases where the DR and UR of a target sequence are separated by at least one nucleotide, the ligation step can be preceded by (b0) extending the DR' using the sample as a template so the extended DR' and UR' become adjacent and can be ligated. The ligation product can then be detected by a variety of means; if desired, the products can be amplified prior to detection. Various detection TempO-Seq™ methods are disclosed herein.

Samples

The samples used in the method can be any substance where it is desired to detect whether a target sequence of a nucleic acid of interest is present. Such substances are typically biological in origin, but can be from artificially created or environmental samples. Biological samples can be from living or dead animals, plants, yeast and other microorganisms, prokaryotes, or cell lines thereof. Particular examples of animals include human, primates, dog, rat, mouse, zebrafish, fruit flies (such as *Drosophila melanogaster*), various worms (such as *Caenorhabditis elegans*) and any other animals studied in laboratories or as animal models of disease. The samples can be in the form of whole organisms or systems, tissue samples, cell samples, subcellular organelles or processes, or samples that are cell-free, including but not limited to solids, fluids, exosomes and other particles. Particular examples are cancer cells, induced pluripotent stem cells (iPSCs), primary hepatocytes, and lymphocytes and subpopulations thereof. The samples can be provided in liquid phase, such as cell-free homogenates or liquid media from tissue cultures, or nonadherent cells in suspension, tissue fragments or homogenates, or in solid phase, such as when the sample is mounted on a slide or in the form of formalin-fixed paraffin-embedded (FFPE) tissue or cells, as a fixed sample of any type, or when cells are grown on or in a surface, as long as detectors can be put into contact for potential hybridization with the sample nucleic acids. An optional step in the methods of the invention is deparaffinization, especially for FFPE samples.

Nucleic Acids

The nucleic acids of interest to be detected in samples include the genome, transcriptome, and other functional sets of nucleic acids, and subsets and fractions thereof. The nucleic acids of interest can be DNA, such as nuclear or mitochondrial DNA, or cDNA that is reverse transcribed from RNA. The sequence of interest can also be from RNA, such as mRNA, rRNA, tRNA, siRNAs (e.g., small interfering RNAs, small inhibitory RNAs, and synthetic inhibitory RNAs), antisense RNAs, circular RNAs, or long noncoding RNAs, circular RNA, or modified RNA, and can include unnatural or nonnaturally occurring bases. The nucleic acids can include modified bases, such as by methylation, and the assay is designed to detect such modifications. The nucleic acid of interest can be a microRNA (miRNA) at any stage of processing, such as a primary microRNA (pri-miRNA), precursor microRNA (pre-miRNA), a hairpin-forming microRNA variant (miRNA*), or a mature miRNA.

Relatively short nucleic acids of interest, such as mature miRNAs, can be lengthened to enhance hybridization to the detectors. For example, many microRNAs are phosphorylated at one end, and can be lengthened by chemical or enzymatic ligation with a supplementary oligo. The supplemental oligo can be single-stranded, double-stranded, or partially double-stranded, depending on the ligation method to be used. If desired, the supplemental oligo can be unique to each target sequence, or can be generic to some or all of the target sequences being ligated. The detectors can then be designed with extended DR' and/or UR' regions that include a portion that hybridizes to the supplemental sequence. A target sequence can also be supplemented by adding nucleotides, such as by polyadenylation, where the extended detectors include at least a portion to hybridize to the supplemental polyA tail.

The amount of nucleic acid in the sample will vary on the type of sample, the complexity, and relative purity of the sample. Because of the sensitivity of the assay, the sample can be taken from a small number of cells, for example from fewer than 100,000, 10,000, 1000, 100, 50, 20, 10, 5, or even from a single cell or a subcellular portion of a cell. The total amount of nucleic acid in the sample can also be quite small: less than 100, 50, 20, 10, 5, 2, 1 micrograms, 500, 200, 100, 50, 20, 10, 5, 2, 1, 0.5, 0.2, 0.1 nanogram, 50, 20, 10, 5, 2, 1 picogram or less of nucleic acid (see FIG. 6d), or less than 10, 1, 0.1, 0.01, 0.001 picograms of nucleic acid, or amount of a lysate containing equivalent amounts of nucleic acid. The copy number of a particular target sequence can be less than 100,000, 10,000, 1000, 100, 50, 20, 10, 5, or even a single copy present in the sample, particularly when coupled with representative amplification of the ligation product for detection. The amount of input nucleic acid will also vary, of course, depending on the complexity of the sample and the number of target sequences to be detected.

Selection of Target Sequences for Design of Detectors

The target sequences can be selected from any combination of sequences or subsequences in the genome or transcriptome of a species or an environment, or modified nucleic acids or nucleic acid mimics to which the detector oligos can bind or hybridize. The set can be specific for a sample type, such as a cell or tissue type. For some sample types, the number of target sequences can range in any combination of upper and lower limits of 1, 2, 5, 10, 20, 50, 100, 200, 500, 1000, 2000, 5000, 10,000, 20,000, 23,000, 30,000, 38,000, 40,000, 50,000, or more. The number of target sequences can also be expressed as a percentage of the total number of a defined set of sequences, such as the RNAs in the human transcriptome or genes in the human genome, ranging in any combination of upper and lower limits of 0.1%, 0.2%, 0.5%, 1%, 2%, 5%, 10%, 20%, 25%, 30%, 35%, 40%, 45%, 50%, 65%, 60%, 70%, 75%, 80%, 85%, 90%, 95%, and 100%. Where large sets of detector oligos are used, it can be useful to check the full sequence of each oligo for potential cross-hybridization to other oligos in the set, where, for example, one oligo may inadvertently serve as an template to other detectors. While such non-specific artifacts can be identified by sequence, and are typically discarded from detection results, they may represent noninformative hybridization events that compete for reaction resources.

The target sequence of interest can be a subsequence of any cancer-associated marker, such as any of genes listed in Tables 1, 2, and 3.

Detector Oligonucleotides

Based on the particular target sequences, the invention provides pools of detector oligos where a target sequence has a pair of upstream and downstream detectors (UD and DD) that correspond to DR and UR, which are typically subsequences of the entire nucleic acid sequence of interest. Detector oligos can be designed to hybridize to the target sequence so a single-stranded sequence portion of the target sequence remains between the detectors, which can then be filled in, such as by reverse transcriptase or polymerase, thereby extending a detector to bring it effectively together with the other detector so they can be ligated.

Detectors can be provided to detect targets that contain mutations including individual single-nucleotide polymorphisms (SNPs), gene fusions, and exon-splicing variants, or modifications such as pseudouridylation and methylation. For example, DNA samples of interest can have bases that are methylated, such as $N^6$-methyladenine ($m^6A$). DNA from mammals and other species can have one or more 5-methylcytosine ($m^5C$) modified bases, often appearing in GC, CHH and CpG dinucleotides, which sometimes form CpG-rich islands. For RNA samples, modifications to be detected by the invention include methylated ribonucleotides having $m^6A$ (often playing a role in mRNA regulation), $m^5C$, and $N^1$-methyladenosine ($m^1A$), which can be dynamically modified in mRNAs and is sometimes correlated with protein translation.

Detectors can contain blocking groups, modified linkages between bases, unnatural or nonnaturally occurring bases or other unnatural or nonnaturally occurring components. An individual target sequence can have more than one set of DRs and URs, which can be selected by the user to optimize the performance of the assay. Multiple sets of DRs and URs can provide multiple measurements of the same target sequence or of different portions of the target sequence, such as different exons or exon junctions, or provide measurement of a portion of sequence that is not mutated versus a portion of sequence that may harbor a mutation.

The detector oligos themselves can be DNA, RNA, or a mixture or hybrid of both. If desired, they can have a modified nucleotide such as dideoxy nucleotides, deoxyUridine (dU), 5-methylCytosine (5mC), 5-hydroxymethylCytosine (5hmC), 5-formylCytosine (5fC), 5-carboxylCytosine (5caC), and Inosine. Yet other modifications to detector oligos include modified bases such as 2,6-diaminopurine, 2-aminopurine, 2-fluro bases, 5-bromoUracil, or 5-nitroindole. Other detector oligos can have a modified sugar-phosphate backbone at one or more positions. Such modifications include a 3'-3' or 5'-5' linkage inversion, a locked nucleic acid (LNA), or a peptide nucleic acid (PNA) backbone. LNAs can be useful for their stronger hybridization properties to complementary bases, enhancing the selectivity or the overall binding affinity for the detector oligo as a whole. The modified bases or bonds can also be used at positions 1, 2, or 3 away from the point of ligation.

As shown schematically in FIG. 1, a downstream detector (DD) has a complementary downstream region (DR'), which can be at least 4, 6, 8, 10, 12, 14, 16, 18, 20, 22, 24, 26, 28, 30, 35, 40, 45, or 50 nucleotides in length. Similarly, an upstream detector (UD) has a complementary upstream region (UR'), which can be at least 4, 6, 8, 10, 12, 14, 16, 18, 20, 22, 24, 26, 28, 30, 35, 40, 45, or 50 nucleotides in length. In a given pair of DD and UD for a target sequence, the DR' and UR' need not be exactly the same length, but will typically be similar so they can hybridize to the target under similar conditions and stringency.

As discussed in more detail below, the detectors can be optimized for ligation, such as by providing a 5'-phosphate on the UD, although this is not necessary, depending on the selection of ligase or other ligation methods. Ribonucleotides can also be substituted at the ligatable ends of the DD and UD to increase the specificity and efficiency of ligation, as when an RNA ligase is used.

Anchored Detectors

In one configuration of the TempO-Seq™ assay, the upstream detector has a second region (UR2') that is complementary to a second region of the target sequence (UR2), as illustrated in FIG. 2a. Because the tail of the UD can hybridize to a separate portion of the target, this configuration can be described as an "anchored" detector, as in FIG. 2b. The anchor at the 3' end of the UD hybridizes with the target to form a double-strand and is thus configured to resist digestion to nucleases that degrade single strands, such as 3' exonucleases like exo I.

As a separate target-binding region, the anchor UR2' can be used to provide additional discrimination between similar sequences, such as isoforms of a family of genes where sequence differences between isoforms are found beyond the range of the DR and UR target sequence. The UR2' can be at least 4, 6, 8, 10, 12, 14, 16, 18, 20, 22, 24, 26, 28, 30, 35, 40, 45, or 50 nucleotides in length. The UR2' can be separated from the UR' by a noncomplementary region (CP1), which can be at least 8, 10, 12, 14, 16, 18, 20, 22, 24, 26, 28, 30, 35, 40, 45, 50, 60, 70, 80, 90, or 100 nucleotides in length. In general, the UR2' will be upstream relative to the UR'. If an amplification region (such as P2') is present, it can be upstream of the UR', such as within the CP1 or part of UR2' to allow amplification of the UR' portion as shown in FIG. 2c to generate the amplification products (AP) in FIG. 2d.

In a mirror-image configuration, it is the downstream detector that has the anchor region (DR2') complementary to a second region of the target sequence. The DR2' anchor hybridizes to a DR2 on the target so that the configuration resists the action of 5' ss-exonucleases. The UR2' of the DD will generally be downstream relative to the UR'. If an amplification region (such as P1) is present, it can be downstream of the DR' to allow amplification of the DR' after ligation. Anchored DDs and UDs can be used separately or in combination to resist a cocktail of nucleases.

Because the separate anchor region of the detector can affect the hybridization characteristics of the detector via monomolecular kinetics, the compositions and relative lengths of the DR2', CP1(s), DR', UR' and UR2' can be tuned to optimize target selectivity between the detector pair and among the pairs of the detector pool.

Detectors that are not used in the ligation reaction can be degraded as shown in FIG. 2e. Moreover, incompletely bound detectors, such as those in FIG. 2f, can also be degraded, for example when the UR' of a UD binds to the UR of a target, but the UR2' does not bind, whether because the UR' is bound to a non-target sequence or to a target that was related to the intended target UR but lacked a UR2. Similarly, an anchored DD that binds a DR2 but not the DR of a target will be susceptible to a 3' ss-exonuclease (or will not generate a valid ligation product with a corresponding UD). Other detectors will fail to be amplified, for example detectors in excess of target sequence in the sample or detectors that are bound nonspecifically to nontarget sequences. The use of anchored detectors can therefore increase the specificity of the ligation assay for target sequences while allowing nucleases to degrade excess or unused detectors.

Blocked Detectors

Another configuration has detectors that are nuclease-resistant by having a nuclease-blocking group at or adjacent to one end. FIG. 2h shows a DD, having a 5'-blocking group, that can be used in combination with a 5' exonuclease. Also shown is a UD having a 3'-blocking group for use with a 3' exonuclease. Preferably when a 5' or 3' exonuclease is used where there are multiple targets and pairs of detectors, all of the downstream or upstream detectors have a 5' or 3' block, respectively.

Useful configurations for resisting nucleases include termination with an inverted nucleotide such as deoxythymidine (idT), a dideoxynucleotide such as dideoxythymidine (ddT or iddT), or 2'/3'-acetyation of the terminal nucleotide. Depending on the substrate preferences of the nuclease selected, one or more of the other modified nucleotides described earlier can be used as a blocking group. Alternatively, one or more of the terminal nucleotides are attached to the rest of the oligo via one or more phosphorothioate bonds instead of naturally occurring phosphodiester bonds. Other modifications that may resist a nuclease include the LNA or PNA backbones discussed earlier. In some configurations, a hairpin loop or other secondary structure on the detector can serve as the nuclease-blocking group for a detector. One end of the hairpin can have a blocking group. In other configurations, prior to hybridization, a protein or other component can be bound the 5' end of a DD or the 3' end of a UD, such as a sequence-specific single-strand-binding protein like a far upstream element (FUSE) binding protein (FUBP) via a ssFUSE sequence incorporated into a detector. If the 5' end of a DD or the 3' end of a UD detector is configured to be immobilized, whether permanently or reversibly, to a solid phase, the solid phase itself can serve as a block against nuclease activity on the detector. It can be useful to combine any of the preceding features in a single detector or both detectors to resist the action of the nuclease selected and to provide other advantages, such as stability and hybridization properties.

Protectors

Yet another configuration provides one or more oligos that protect the detectors by hybridizing to the DD or UD at a region that will not interfere with hybridization of the DR' or UR' regions complementary to the target sequence. For example in FIG. 2i, a DR2 protector oligo is provided to hybridize to a DR2' region at the 5' end of the DD, forming a double-stranded configuration (indicated by a brace) that is resistant to 5' exonucleases. If a 3' exonuclease is to be used, then a UR2 protector can be provided to form a double-strand at the 3' end of the UD. The protector oligos can themselves be protected from exonuclease activity by a blocking group or bond as described above. For example, a 3'-blocked UR2 protector is shown in FIG. 2i, and a 5'-blocked DR2 protector is shown in FIG. 2j. If a cocktail of 5' and 3' exonucleases is to be used, then both DR2 and UR2 protectors can be provided, optionally with 5'- or 3'-blocking groups, respectively.

Detector Labels

Where the ligation assay proceeds directly to a detection step, either or both detectors can be designed to be labeled appropriately for detection. For example, the detector can be conjugated to any number of molecular or physical entities, labeled with a crosslinker, activatable crosslinker, activatable cleavage group or enzymatically cleavable group, optical, color or fluorescent dye, latex or other beads, quantum dots, or nanodots, or nanoparticles. Any of these entities can also be further modified or conjugated to other entities. The label can also take the form of an additional nucleotide sequence that serves to enable detection and identification, such as a barcode sequence. For example, a useful barcode sequence can uniquely identify the specific gene or target sequence, or a group of select genes or target sequences within the sample that are being measured. Such sequences can be positioned between the UR' and P2' sequence, and/or between the DR' and P1 sequence, so they are amplified when using flanking primers. This sequence can also be a random sequence, useful for identifying the number of copies of the target gene in the sample, independent of the particular efficiency of any amplification step.

Cleavable Detectors

It can be desirable for a detector oligo to contain one or other modifications that can be selectively cleaved by treatment after the ligation or optional amplification step. For example, a detector oligo can have a dU located so that it will not interfere with hybridization or ligation steps. After ligation, however, products incorporating the dU oligo can then be cleaved by dU-specific enzymes, such as uracil-DNA glycosylase followed by endonuclease VIII. Another selectively cleavable site can be a restriction enzyme cleavage site that is not present in the target sequences to be detected. Yet another cleavage site is a photocleavable site. It may also be useful to incorporate a moiety that can be crosslinked before or after ligation, such as a photoactivatable or chemically activatable crosslinker.

Multiple Detectors for a Gene

Multiple detector oligo (DO) sets targeting different sequences within a gene can be designed and synthesized for use to detect that gene. Each DO set hybridizes to its targeted sequence independently of the hybridization of other DO sets to each of their respective targeted sequences. Thus, the statistical reliability, statistical power, of measurement of the gene itself can be increased by use of multiple DO set targeting that gene. Measurement CVs can be reduced. Furthermore, if secondary structure, protein binding, or other factor modulates the hybridization of one DO set, and thus affects resulting measure of gene abundance by that DO set, then the counts from other DOs unaffected by such factors can be used to provide more accurate measure of gene abundance. Outlier analysis can be used to identify such deviations of DO set measurements. In the case that the expression of a gene is low abundant, or that the amount of sample is small, such as from a single cell, and thus the number of gene molecules is low, hybridization of a specific DO set to that low amount of gene may not be sufficient to provide an amplifiable ligated product every time across repeat samples, and hence, not produce sequencing counts from some samples. The use of additional DO sets targeting other sequences within the same gene increases the probability that some of those DO sets will produce counts if the gene is actually expressed, and thus use of multiple DO sets can be used to increase the sensitivity of measurement of low expressed, or low numbers of gene molecules in a sample. The no sample background counts can be used to validate that DO counts result from the presence of the gene even though not all DO sets produce counts. The concurrence of more than one DO set reporting the presence of the gene can be used as a measure to validate that the DO counts result from the presence of the gene even though not all DO sets produce counts. Because the DO sets have a defined sequence, each DO set measurement represents independent measurements of defined target sequences, permitting statistical methods to be applied to determine that a gene is expressed or present in the sample or not.

Detecting Modified Nucleotides

In a particular embodiment, multiple detectors can be used to detect the presence or absence of modifications to a nucleic acid. For example, a first pair of detectors can be directed to a first target sequence of a full-length nucleic acid of interest, such as an mRNA, where the first target sequence is suspected of having a modification, such as methylation, at a particular position for interrogation. The first pair of detectors may yield one detection result (e.g. generation of an analytical ligation product or amplicon) when the modification is present at the position, and yield a different detection result (e.g. no analytical product) when the modification is absent from the same position. Detectors, which are directed to one or more different target sequences or positions of the full-length nucleic acid, can be used as a positive control for the presence of the full-length nucleic acid.

Hybridization

Returning to the steps of the assay, the detectors are provided so that they contact the sample to allow the detectors to hybridize specifically to the target nucleic acids. Hybridization conditions can be selected by the skilled artisan to allow and optimize for hybridization between the polynucleotides with the desired degree of specificity or mismatches, and such conditions will vary with the lengths and compositions of sequences present in the hybridization reaction, the nature of any modifications, as well as conditions such as the concentrations of the polynucleotides and ionic strength. Particular hybridization temperatures include 30°, 32.5°, 35°, 37.5°, 40°, 42.5°, 45°, 47.5°, 50°, 52.5°, 55°, 57.5°, 60°, 62.5°, 65°, 67.5°, 70°, 72.5°, 75°, 77.5°, 80°, 82.5°, 85°, 87.5°, and/or 90°. Particular hybridization temperatures can be achieved by ramping the temperature up or down at various rates and profiles, such as timed temperature plateaus, one or more incremental increases or decreases of 5° C., 10° C., or 15° C., and repeated cycling between two or more temperatures. Ions such as $Li^+$, $Na^+$, $K^+$, $Ca^{2+}$, $Mg^{2+}$ and/or $Mn^{2+}$ can also be present from 0, 1, 2, 5, 10, 20, 50, 100, 200, and 500 mM, and such ions can affect the selection of the other hybridization conditions. Hybridization is also affected by steric crowding components such as branched polysaccharides, glycerol, and polyethylene glycol. Further additives can be present in the hybridization (and subsequent) reactions, such as DMSO, non-ionic detergents, betaine, ethylene glycol, 1,2-propanediol, formamide, tetramethyl ammonium chloride (TMAC), and/or proteins such as bovine serum albumin (BSA), according to the desired specificity.

Optionally, the conditions for hybridization can be adjusted or fine-tuned to permit other steps to be performed in the same environment. For example, the same buffers used for hybridization can be used for lysing cells in a sample, promoting hybridization of certain cell types, facilitating removal or permeation of cell walls, cell membranes, or subcellular fractions, as desired. Depending on the ligation method used in the assay, hybridization conditions can be selected to be compatible with conditions for ligation as is, or with the addition of one or more components and preferably without requiring a change of the reaction container when transitioning from hybridization to ligation steps.

Ligation

The ligation reaction can occur by chemical ligation or by using a ligase enzyme or a ligation-facilitating co-factor. A variety of nick-repairing ligases are commercially available to catalyze the formation of a phosphodiester bond between adjacent single-stranded polynucleotides when hybridized to another single-stranded template, such as to join DNA to RNA when hybridized to template. An example is bacteriophage T4 DNA ligase, which is generally understood to use ATP as a co-factor. The ATP can be supplied during the ligase reaction. In other reactions, the ligase can be pre-adenylated. In yet other reactions, the UD must be pre-adenylated at the 5' end, as with a 5' App DNA/RNA ligase. The UD in a typical reaction will have a 5'-phosphate to facilitate ligation to the DD, although this is not necessary, depending on the selection of ligase and ligation conditions. (Where a 5'-phosphate on the DD is required for efficient ligation, using a comparable oligonucleotide without 5'-phosphorylation can be used to inhibit or reduce undesired ligation.) Preferred ligation conditions include 10, 25, 50, 100 mM Tris-HCl (pH 7.5, 8.0, or 8.5); at least 10 mM, 5 mM, 2 mM, 1 mM $MgCl_2$; at least or at most 2 mM, 1 mM, 0.7 mM, 0.5 mM, 0.2 mM, 0.1 mM, 0.05 mM, 0.02 mM, 0.01 mM, 0.005 mM, 0.002 mM, or 0.001 mM ATP; or at least 10 mM, 7 mM, 5 mM, 2 mM, 1 mM, 0.5 mM DTT or other antioxidant. T3 DNA ligase can also be used, which can ligate a broader range of substrates and has a wider tolerance for salt concentration. As with other steps, the temperature can be selected according to the characteristics of the reaction components and conditions such as ionic strength.

As discussed above, the ligation step can be preceded by an optional extension step, as in FIG. 1, step (b0). The ligation step can also be preceded by an optional cleavage step, such as by a nuclease, to remove any overhangs. In other cases, a portion of the DD can overlap with the UR sequence to which the UD hybridizes, so that after hybridization of the UD and the DD, there is an overhang sequence of 1, 2, 3, or more bases. A useful enzyme for removing an overhang is a Flap endonuclease, such as Fen-1, which cleavage leaves a ligatable 5'-phosphate.

Amplification

If desired, the ligation product can be amplified (for example by PCR or qPCR) to facilitate detection. Amplification methods and instruments are commercially available, including PCR plate and droplet formats, and the amplification enzymes (such as Taq and its commercial variants) and reaction conditions can be selected and tailored to the particular platform. Optionally, the polymerase selected for amplification can have strand-displacing activity. As illustrated in FIG. 1, the detectors can have additional sequences ("tails") including primer hybridization sequences (e.g. P1, P2') or complements thereof, that serve as amplification sequences, so that after ligation, the ligation product can be amplified with a pair of amplification primers (P1, P2).

Amplification can also be linear, or achieved by any number of methods other than PCR. If desired, the amplification primer can incorporate a barcode sequence, for example a barcode sequence that uniquely identifies the sample in a multi-sample experiment, and optionally has redundant and/or error-correction features. In some experiments, for example, different sample barcodes can be used for 96, 384, 1536, or more generally $2^n$ or $4^n$ different samples that are prepared with different barcodes separately for some steps, such as hybridization, ligation, and amplification, and combined for others, such as detection. The barcode sequence can be incorporated into the primer, such as 3' to the amplification sequence, so that the barcode becomes part of the amplified strand. In other instances, the amplification sequence of the primer can be extended by an additional sequence to provide a primer hybridization sequence that can be used for use in subsequent sequencing steps. The barcode may also be interposed between the amplification sequence, and if desired, the extended amplification sequence, and another sequence that can be used for capture, such as capture onto a surface as part of a sequencing process, and/or for yet another primer hybridization sequence that is used for sequencing. In each case the barcode will be amplified with the rest of the detector sequences, for instance forming a single amplified, elongated molecule that contains sequencing primer hybridization sequences, sample barcode, and a gene-specific sequence, which may include a gene-specific barcode or a target molecule-specific barcode as well as sequence or complement to the sequence of the target gene. In the case where the targeted oligo is a cDNA, a gene-specific sequence or a sample-specific sequence can be added as part of the primer used for reverse transcription, and be a part of the sequence targeted by the UD and DD.

In other instances, methods known in the art can be used to amplify the ligated DD and UD sequences, such as by repetitive cycles of (1) ligation, (2) heating to melt off the ligated product, (3) cooling to permit hybridization of DD and UD to the target, (4) ligation, then repeating the heating (2), cooling (3), and ligation (4) steps. These additional amplification steps can be performed before amplification step (c), during which the sample barcodes and other sequences are added to the ligated UD and DD sequence. The target of the UD and DD hybridization may also be amplified by whole transcriptome amplification of RNA or amplification of cDNA.

Detection

The ligation product (or its amplicons) can optionally be detected by methods such as sequencing, qPCR, end point PCR, enzymatic, optical, or labeling for detection on an array or other molecule detection. Other detection methods include flow-through systems for counting labeled molecules. Depending on the detection method, the skilled user will be able to modify the design of the detectors and amplification primers to include functional features that are appropriate, such as for bridge amplification on a sequencing flow cell. The experimental resources used for amplification and detection can be limited and are often among the most expensive, and their consumption can be optimized by reducing the number of non-informative assay components present at various stages of the assay.

Nucleases

Accordingly, the invention provides optional nucleases and assay components that are configured to resist degradation to enable more efficient use of resources and more sensitive detection. As a further advantage, the invention enables a simpler assay workflow that can be performed in a single reaction container or entirely in liquid phase.

The nuclease can be an enzyme that digests or degrades single strands of nucleic acids. Preferably the nuclease does not digest (or has significantly less activity on) double strands, including DNA:RNA hybrids. For example, the nuclease can have less than 10%, 5%, 2%, 1%, 0.5%, 0.2%, or 0.1% the activity on double strands compared to single-strands on a molar substrate ratio under the same conditions. Similarly, the nuclease can be selected so it does not appreciably digest at single-stranded nicks in a double-strand. The nuclease can be an endonuclease that degrades single strands, such as mung bean nuclease under certain conditions. The nuclease can also be an exonuclease that degrades single strands, which can be single strands of DNA. For example, a nuclease having single-stranded 3'-to-5' exonuclease (3' exo) activity includes Exonuclease I from *E. coli* (exo I) and T3 exonuclease. Enzymes such as exonuclease T (RNase T), which has 3' exo activity on DNA and RNA single strands, can be used as long as the detectors have been ligated and the RNA strands are no longer needed in the assay. Nucleases having single-stranded 5'-to-3' exonuclease activity include exonuclease VIII and RecJ$_f$. The nuclease can be an enzyme that digests 5' overhangs or flaps, such as Flap endonuclease 1. Nucleases can be used singly or in a cocktail of nucleases, such as a pair of 3' and 5' exonucleases.

The nucleases can be used at various stages of the assay. For example, a nuclease can be provided (b2) after the ligation step (b1) to remove unligated or excess detectors, as in FIG. 2*e*. The nuclease can also degrade detectors that are only partially or nonspecifically hybridized to target sequences, as in FIG. 2*f*. If compatible with the ligation conditions used, the nuclease can also be provided during the ligation step (b1 and b2 together), or even before the ligation step (b2, then b1) as long as it does not interfere with the intended detection of target sequences. Depending on the assay design, the nuclease can be provided before, during, or after the optional (b0) extension and (d) amplification steps, or at multiple steps to effect the desired purpose of removing undesired target, detectors, other oligos, or any products.

When the nuclease activity is no longer desired, the nucleases can be removed or inactivated, such as after the ligation step. Nucleases can be inactivated by methods selected for a particular nuclease but will not substantially interfere with the rest of the assay. For some nucleases, a nuclease inhibitor (as in FIG. 4, lower right) or chelating agent, such as EDTA, can be added as long as it does not interfere with (or can be removed prior to) a subsequent step that may require Mg$^{++}$ for example. Other nucleases can be inactivated by heat, for example single or repeated incubation at 70° C., 75° C., 80° C., 85° C., 90° C., 95° C. or 98° C., for 1, 2, 5, 10, 15, 20, 25, 30, 45 minutes, or 1 hour. If more than one nuclease is used, either or both may be inactivated individually or by the same means. To resist the activity of nucleases provided at one or more steps of the invention, components of the assay are provided by the invention in various configurations that permit detection of target sequences. Selection of the configuration method will depend, of course, on the particular nuclease being used.

Steps in Solid and/or Liquid Phases

In other embodiments, one or more of the steps can be performed in liquid phase, such as in a microfluidic system, so that one or more of the steps does not involve capture to a solid phase, such as to a bead or a plate surface. For example, any one or combination of the hybridization, extension, ligation, nuclease digestion, amplification, or detection steps can be performed in liquid phase.

In some embodiments, the sample is provided in a solid phase, such as an FFPE, so that it remains in solid phase for one or more steps of the detection process. When in solid phase, the sample can be washed between steps to remove unused assay components or to reduce background, for example after hybridization or after ligation.

In a mixed phase assay, a solid phase can be used to immobilize one or more of the sample, the detector oligos, the hybridization complex, the extension product, the ligation product, or the amplification product. In particular, the target nucleic acid can be attached to a solid surface during the hybridization step, the ligation step, or both. The solid surface can be a bead, such as a magnetic, nonmagnetic, polymeric, reversible immobilization, or latex bead, or compound beads thereof, or a relatively flat surface such as a plate or flowcell surface, optionally with coatings of similar materials. The mixed phase format allows the components to be transferred from one reaction environment to another, or the conditions to be changed as the components remain in one container.

Adding Successively to the Same Reaction Container

Alternatively, the reactions can be optimized so that at least one of steps is performed by adding reagent, such as an enzyme or buffer component, successively, so that a reaction takes place in the same container as the preceding step, optionally without requiring an intervening wash or transfer step. Preferably, the sequence of additions does not require significant additions of liquid volumes to dilute the components for the next reaction, for example no more than 1-, 1.5-, 2-, 2.5-, 3-, 5-, 10-, 15-, or 20-fold dilution between the initial sample and preparation for detection. The components to be added can be provided in a kit, as described below.

Steps in Situ; Cross-Linking, Photocleavage, Elution

In some embodiments, the hybridization, ligation, or extension steps can be performed while the target sequence is in situ, as with FFPE samples. This can be particularly useful, for example, when the sample is on a histological slide, so that the ligation is known to occur at a recordable location and can be compared to similar reactions at other locations on the slide. It useful for any sample where the target sequence is part of a nucleic acid is fixed to the tissue. The ligated probes can remain at the location while other steps are performed, such as imaging or detection of other analytes at or near the location. These other analytes can be any of the nucleic acids described herein, including modified nucleotides, carbohydrates or lectins, proteins and other antigens, and any other stainable molecule or feature that can be visualized. These other analytes in situ can be present on the surface of the sample, treated to expose them on the surface, or be made accessible to reagents such as stains to aid their visualization, such as by permeabilization.

If desired, the ligated probes can remain in situ more securely by a variety of chemical or enzymatic methods for cross-linking to the site, which can be permanent or reversible, such as by a photocleavable link as with using a cyanovinylcarbazole nucleoside analog ($^{CNV}$K). The area to be photocleaved can be any shape or size, and can be focused on one or a few selected cells of interest, or can focus on a histological or pathological feature. The photocleavage steps may also be performed whether the sample is wet or dry.

In a particular embodiment, the ligation products can be eluted from the sample in situ for collection and further processing, preferably eluting from small areas to preserve the location information and morphological context of the ligation reaction products. Elution can simply be by heat in low salt, effected by the PCR process, or by addition of base. The eluted area can be smaller than 2 mm$^2$, 1, 0.5, 0.2, 0.1, 0.05, 0.02, 0.01, 0.005, 0.002, 0.001 mm$^2$ (1000 µm$^2$), 500 µm$^2$, which covers the range of single human cells of many types.

Photocleavage and elution steps can be coordinated so a first area is photocleaved, followed by elution of a second area. The first and second areas can be coextensive, overlap, or be larger or smaller relative to each other. In other combinations, an area may first be nonspecifically washed or selectively eluted for some components, then photocleaved, followed by elution and collection of other components.

In a particular embodiment, samples are dried, fixed, optionally permeabilized, and optionally processed prior to or during the assay. In yet another embodiment, samples are simply preserved by fixation before the assay.

TempO-Seq™ Assays

Standard Version

A "standard" version of the TempO-Seq™ assay provides a method for detecting target nucleic acid sequences in a sample, wherein a target sequence has a downstream region (DR) and an upstream region (UR). The steps include (a) contacting the sample with a pair of detector oligos. The detector pair comprises a downstream detector oligo (DD) having a complementary downstream region (DR') and a separate upstream detector oligo (UD) having a complementary upstream region (UR'). At least one of the DD or UD has a second complementary region (DR2' or UR2') separated from the DR' or UR' by a noncomplementary region (CP1) that does not hybridize to the target nucleic acid. Thus, the DR2' or UR2' can specifically hybridize to a DR2 or UR2 of the target nucleic acid. This allows the pair of detectors to hybridize specifically to the target nucleic acids. The method continues by (b1) ligating the DR' and UR' if both are specifically hybridized to the DR and UR of a target sequence; and (b2) exposing hybridization complexes to at least one nuclease that degrades single strands but does not significantly degrade double strands. Thus, nonspecifically hybridized DDs and UDs are degraded by the nuclease. The ligation product serves as an analytical product that indicates the presence of the target sequence in the sample.

In a particular embodiment, the assay targets 50 nucleotide regions in RNAs with pairs of detector oligos (DOs), which share universal PCR primer landing sites. After annealing, the adjacent DOs are ligated together and amplified by PCR (which can also add sample tag sequences and sequencing adapters). A single PCR can primer pair amplify all ligated probes in a single sample. Attaching unique tag sequences that are sample-specific can allow sample pooling into a sequencing library of 384 or more samples per flow cell.

As disclosed above, the sample can be a tissue sample, can be mounted on a slide, or can be an FFPE. The target nucleic acid can be from an FFPE sample, or can be in situ. The standard version can have a step of eluting the ligation product.

Figure 4:
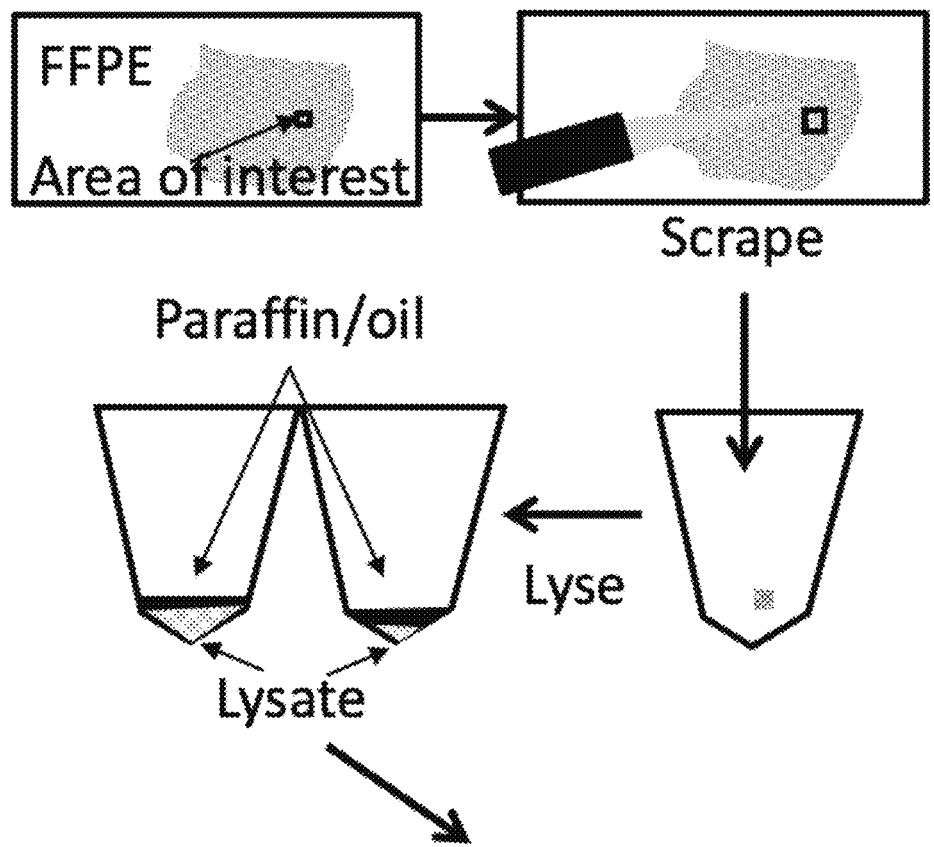
FIG. 4 depicts steps for processing FFPE samples in the "standard" TempO-Seq™ FFPE protocol.

The standard assay can be performed with FFPE samples, as discussed in Example 5 and illustrated in FIG. 4. The TempO-Seq™ assay is commercially available as a kit in a Whole Transcriptome version (BioSpyder Technologies, Inc., Carlsbad, Calif.).

Modified Version of TempO-Seq™ Assay

Figure 3:
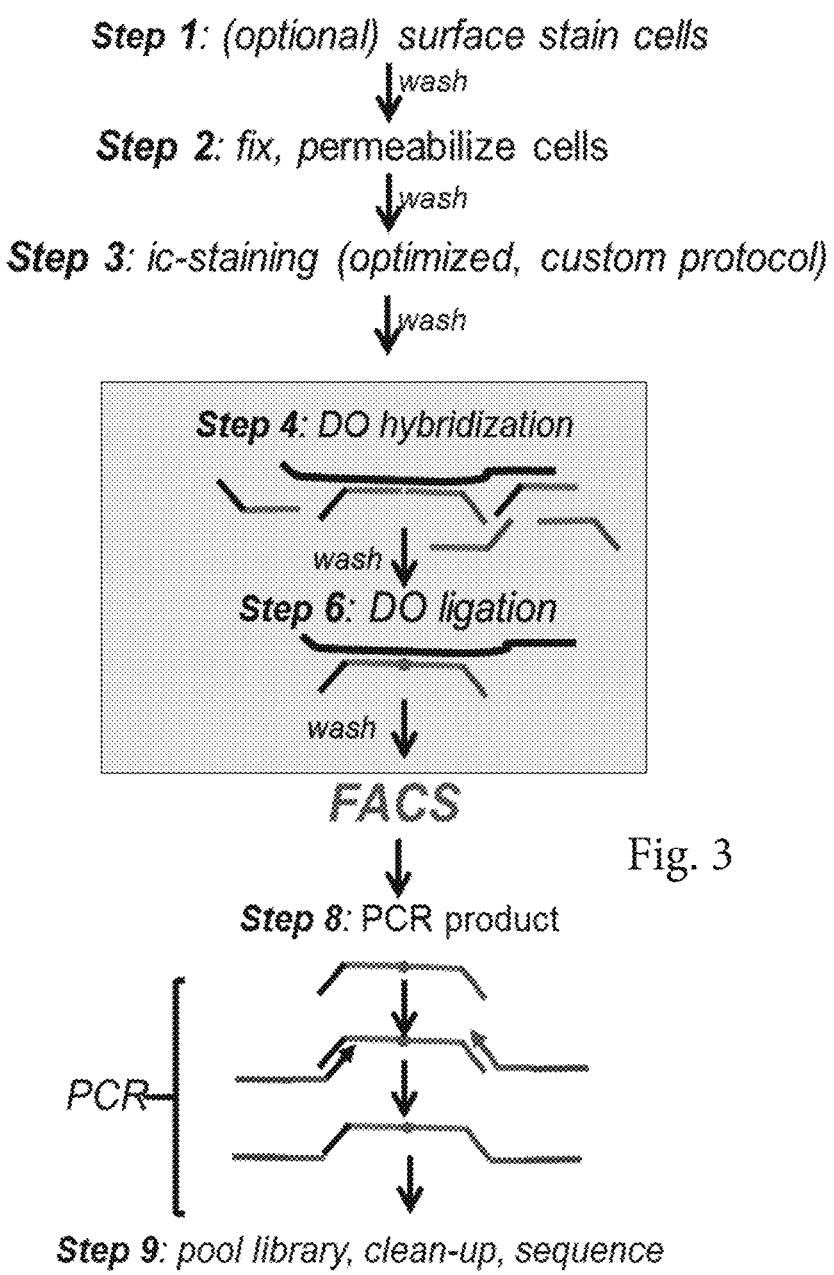
FIG. 3 shows a modified version of the TempO-Seq™ assay that can be performed after antibody-staining, before flow cytometry sorting (FACS) and PCR.

A "modified" version of the assay is described in Example 3 and illustrated in FIG. 3.

in Situ Version of TempO-Seq™ Assay

Figure 6:
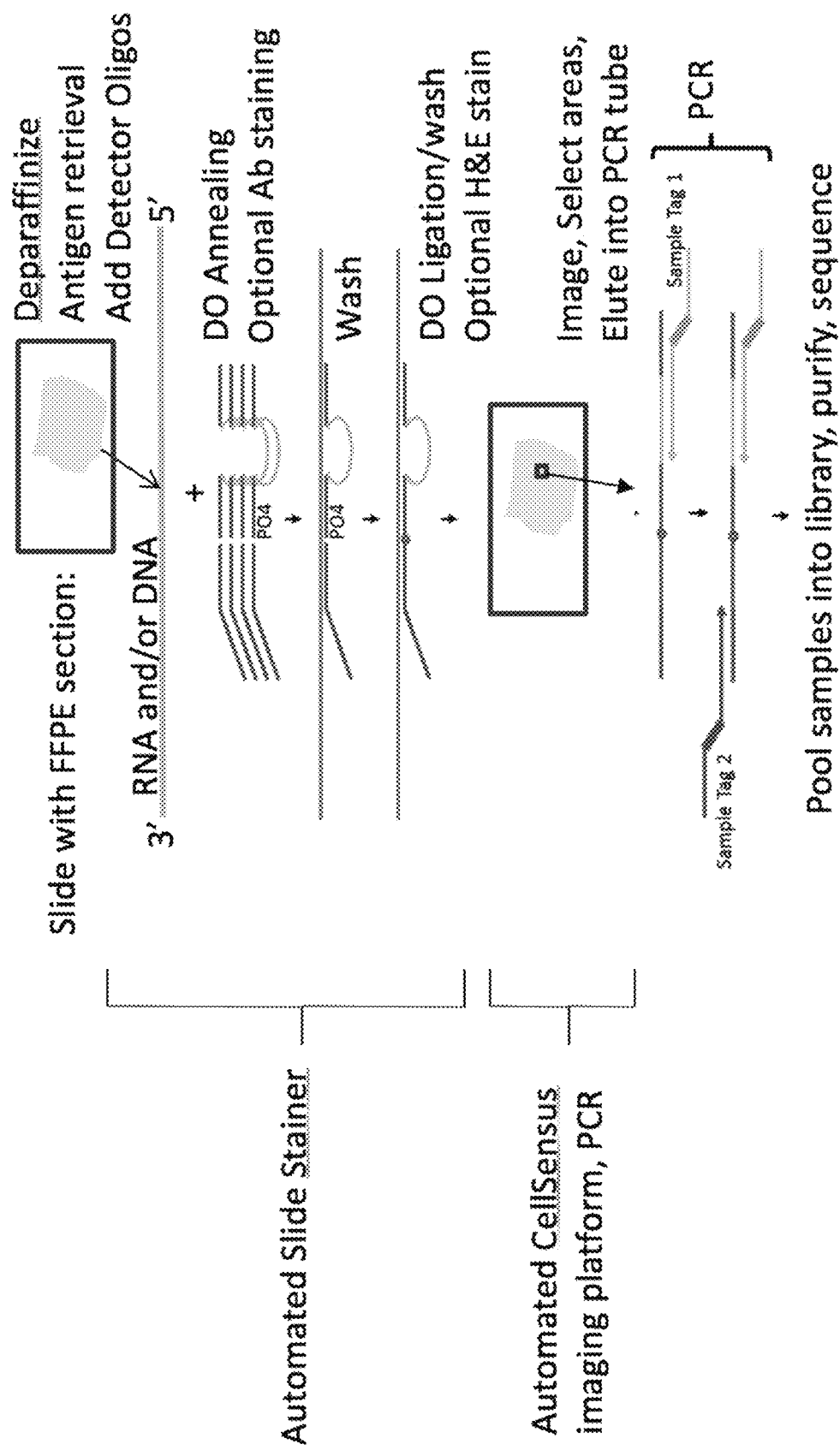
FIG. 6 illustrates an automated in situ assay process.

An in situ version of the assay is described in Example 5 and illustrated in FIG. 6. In this version, probes that are not bound to the sample can be washed away, reducing assay background, and increasing specificity and overall sensitivity. The method can detect a nucleic acid sequence from a selected area of a sample in situ, by performing in any order: imaging the sample for the presence or absence of an analyte; selecting an area of the sample based on the imaging; detecting a target nucleic acid sequence by any of the detection methods for nucleic acid sequences herein; and collecting the ligation products from the selected area for analysis.

The selected area can be a morphological feature, which can be visualized by one or more stains. Any histologic stain can be used to image the sample. Useful stains include fluorescent dyes, enzymes (such as peroxidase or alkaline phosphatase), as well as radioactive labels. Immunostaining or other antibody-based staining methods can be used, including immunohistochemical staining of tissue sections.

The analytes can be any of the nucleic acids or modified versions described herein. More generally, the analytes can be any detectable molecule such as proteins, carbohydrates, or their binding partners or stain components.

The detection of many antigens can be improved by antigen retrieval methods that break some of the protein cross-links that may have form during fixation, thereby uncovering previously hidden antigenic sites. Retrieval methods include heating, such as heat-induced epitope retrieval (HIER) and using enzyme digestion, such as proteolytic induced epitope retrieval (PIER).

Individual steps in this version can be automated or performed manually, or using any slide-staining apparatus where temperature can be controlled during incubations.

Kits

The invention provides kits for performing the methods described above, comprising detector oligos, and optionally a nuclease, a ligase, and/or a polymerase. The kits can further provide reaction buffers for the enzymes in the kit or buffer components to be added to reactions suitable for the enzymes. The component can be suitable for addition to a container for an enzyme reaction to prepare a suitable reaction buffer for the enzyme. The component can also be selected to be compatible with the reaction buffer for the preceding step of the method so that the component can be added to the same container to form a reaction buffer for the next enzyme to be used. Thus, the components can be selected to enable an "add-add-add" strategy for multiple steps of the assay to minimize transfers of sample, oligos, enzymes and/or solutions between separate containers.

The kits can also have eluent solutions suitable for removing oligonucleotides, such as ligated oligonucleotides, from a tissue sample for further analysis. The kits can further have amplification primers suitable for use with the detectors of the kit.

As disclosed above, the kit can have a pair of detector oligos, which pair comprises a downstream detector oligo (DD) having a complementary downstream region (DR') and a separate upstream detector oligo (UD) having a complementary upstream region (UR), wherein at least one of the downstream detector (DD) or the upstream detector (UD) has a second complementary region (DR2' or UR2') separated from the DR' or UR' by a noncomplementary region (CP1) that does not hybridize to the target nucleic acid and that has an amplification region (P1 or P2'), whereby the DR2' or UR2' can specifically hybridize to a DR2 or UR2 of the target nucleic acid, and at least one nuclease. Kits can also include one or more eluent solutions to remove oligos, such as unligated detectors, or in a separate step, to elute ligation products from the tissue sample.

The kits can also contain a stain, such as a histological stain, such as hemotoxylin or eosin. The stain can also have an antibody, such as for immunostaining, for detecting an analyte in the sample, as described herein.

Diagnostic and Other Methods

The present invention provides a method for detecting a neoplastic state of a cell by detecting one or more cancer marker sequence in a cell. As shown in Table 3 below, in a selected are, ligation products of a second cancer marker sequence can be detected in significantly fewer numbers, such as less than 0.1%, 0.05%, 0.02%, 0.01% or 0.005% than the first cancer marker sequence.

The invention provides methods for generating a gene expression profile for a selected area for a plurality of target sequences.

The invention also provides methods for detecting a neoplastic state of a cells in a tissue detecting a plurality cancer marker sequences on cells in two separate areas of the tissue.

The invention further provides methods for diagnosing a disease state wherein the target sequences are detected in the area of a morphological feature.

Instruments

The invention provides instruments, which can be automated, for imaging samples such as FFPEs or slides, selecting focal areas, and eluting to recover analytes from those areas. The instrument can have an imaging component, a component for collecting ligation products from the selected area, and a component for transferring the products to an external container.

An example of the instruments of the invention is the CellSensus™ digital molecular pathology platform. This platform combines a digital imager for slides, and a mechanism for automatically recovering probes from selected areas, and transferring them, for example to PCR tubes. The platform also includes software to control some or all of these functions and perform analysis.

EXAMPLES

Example 1

Representative Ligation Assay

A representative method is provided to illustrate ligation assays. Here, over 100 RNA expression products were detected in a sample of cells using a multiplex assay format. For each expression product, the assay was designed to detect one or more target sequences within the full sequence of the product. For example, in human cells, a GAPDH gene of interest encodes the enzyme glyceraldehyde 3-phosphate dehydrogenase; three different portions within the RNA transcript of the GAPDH gene were independently detected as target sequences. One such RNA target sequence, identified here as GAPDH_2, was where a 5' end was designated "upstream" (underlined) and the 3' end was designated "downstream" for the direction of transcription and translation. A downstream region (DR) was defined as the downstream 25 bases of GAPDH_2, which has a complementary DNA sequence of DR'. The upstream region (UR) was defined as the upstream 25 bases of GAPDH_2, which has a complementary DNA sequence of UR'.

For GAPDH_2, a pair of detectors was designed: a downstream detector (DD) having the DR' sequence, and an upstream detector (UD) having the UR' sequence. Similar pairs were designed for each of the target sequences to provide a pool of detectors for the assay. In this example, all the upstream detectors were phosphorylated at the 5' end.

In this particular example, an amplification step was to be performed later in the experiment using two primers, P1 and P2, so all UDs in the experiment included a primer sequence (P1) and all URs included a complementary primer sequence (P2'). Because amplification is not necessary to the practice of the invention, however, the sequence of the specific primers and primer sequences is a matter of selection to suit the particular amplification method, if used.

At least 10 ng of RNA isolated from human kidney or liver cell lines was placed in a well of a microtiter plate for each assay experiment. To each well was added 20 µL of 2× Binding Cocktail, which contained 5 nM of each detector (providing a final input of 0.1 pmoles per oligo), 100 nM biotinylated oligo(dT)$_{25}$, and 5 µL, streptavidin-coated magnetic beads in a Wash Buffer (40 mM Tris-Cl pH 7.6, 1 M NaCl, 2 mM EDTA disodium, 0.2% SDS).

The plate was heated for 10 min at 65° C. to denature the RNA, then the temperature was ramped down over 40 min to 45° C. to allow the detectors to anneal to the target sequences in the RNA sample. The plate was then transferred to a magnetic base to immobilize the beads, allowing the supernatant, containing unbound and excess detectors, to be aspirated from the wells. The beads were washed at least three times with 50 µL Wash Buffer.

To each well was added 5 Weiss units of T4 DNA ligase in 20 µL, of 1× ligation buffer, as provided by the supplier. After the beads were resuspended by pipette, the plates were incubated for 60 min at 37° C. to allow target-dependent ligation of DDs to UDs as appropriate.

After the ligation reaction, the beads were immobilized and washed twice with 50 µL Wash Buffer. To release the ligated detectors from their RNA targets, the beads were resuspended in 30 µL and incubated for 5 min at 65° C. After incubation, the beads were immobilized, and the supernatant was removed and transferred to a storage plate.

For the optional amplification step, 5 µL, of the supernatant, containing the ligation products, was transferred to a well of a PCR plate. Then 10 µL, of a PCR cocktail was added, containing 0.45 U Taq polymerase, 0.6 µM P1 primer, 0.6 µM P2 primer, 1.5 mM MgCl$_2$, and 200 µM dNTPs. The thermocycler used the following program: 10 min at 94° C., followed by 20 to 25 cycles of 30 sec at 94° C., 30 sec at 58° C., and 30 sec at 72° C. The amplification products were then sequenced according to manufacturer's instructions. This representative ligation assay can be modified as in the following examples.

Example 2

Anchored Detector Designs

Upstream and downstream detector probe oligonucleotides were prepared as in FIGS. 2a and 3a for 24 target sequences identified as breast cancer targets: ACTB_1, TFF1_1, GATA3_3, GAPDH_3, CDH1_1, KRT19_2, TIMP1_2, NFKBIA_1, ESR1_1, VEGFA 3, LAMP1_2, MUC1_3, BAD_3, PTEN_1, BRCA2_1, BCAT2_3, ICAM1_2, IGF2_3, BRCA1_2, EGFR_1, BMP4_1, KIT_3, WNT1_1, and EGF_3 (in descending order of expected counts). The targets were selected for a range of expression covering 6 orders of magnitude from ACTB_1 to EGF_3.

The assay was performed in triplicate with 100, 10, 1, and 0.1 and 0 (control) nanograms of MCF7 total RNA as sample. The detectors were added to the sample in a volume of 1 or 2 and allowed to hybridize by incubating at 65° C. for 10 minutes, ramping down over 20 minutes from 65° to 45° C., then held for 20 minutes at 45° C. Exonuclease I (*E. coli*) was added to the hybridization mixture in 6 μL of 0.5 Units and incubated for 1 hour at 37° C. T4 ligase was added to the mixture in 6 μL of 5 Units and incubated for 1 hour at 37° C. A heat step was performed for 30 minutes at 80° C. The mixture was amplified by adding 2× PCR master mix. The amplification products corresponding to the target sequences were detected and quantificated by qPCR and sequencing.

Example 3

Modified TempO-Seg™ Assay

Defining the nature of stochastic gene expression is important for understanding the regulation of transcription/translation and cell population dynamics. Jurkat cells and human blood lymphocytes (activated ex vivo, fixed, permeabilized, antibody-stained for surface CD4 and CD8, and for intracellular transcription factors FoxP3 and EOMES) were prepared. A modified version of whole transcriptome TempO-Seq™ gene expression assay was performed in situ, and the cells were FACS-sorted into bulk subpopulations or into single cells. In this modified version, the probes were eluted and gene expression was profiled by sequencing. The modified assay (based on the NIEHS S1500 gene-set) measured 2977 genes ("surrogate whole transcriptome" or "surrogate" assay, compared to the more comprehensive TempO-Seq "whole transcriptome" assay), identifying every known signaling pathway. Bulk cell measurements correlated with the summed single cell measurements ($R^2$=0.89 for a bulk preparation of 1000 CD4-/FoxP3-cells versus single cells). The no-sample control background was <0.06 counts, showing that true "off" could be measured. The "abundance" of genes measured in bulk samples correlated to the number of cells in which expression was "on", a measure of the percentage of time that the gene is on. Only 48 genes were expressed all the time in every single cell, while the rest exhibited no expression in one or more cells. It was observed that most genes were either on or off with very little "ramp up" or "ramp down" of expression over the time required to fix the cells and stop RNA synthesis/degradation.

If a simple average is used to compare the single-cell population to the bulk population, the expression behavior of individual cells over time may be masked behind a single average value for the expression of the bulk population as a whole. When the bulk measurement was 10 counts, 247 cells had 0 expression, 6 had a median expression of 500 (average 583), ranging from 149 to 1206 counts, compared to the highest expressed gene, average counts 12,541, range 7,519 to 18,970; only ~16-fold higher. Thus, the concept of single copy gene expression is more complex than previously understood. Rather, low-expressed genes are "off "most of the time, but when "on" they are at relatively high levels in a cell. This in turn drives up "average" expression levels if measured in larger populations of nonactive cells.

FIG. 3 shows a modified version of the TempO-Seq™ assay that can be performed after antibody-staining, before flow cytometry sorting (FACS). A reagent was used to permeabilize the cells, which provided highly sensitive antibody-staining of intracellular antigens. The protocol was carried out by adding a cocktail of detector oligos (DOs) so that there was a pair of DOs that hybridized to each targeted RNA, and when properly hybridized, the two detector oligos butt up against one another, permitting ligation. Wash steps were used to remove excess nonhybridized DOs, and subsequently, unligated DOs. The FACS sorting was performed, capturing each cell into 10 ml of PCR buffer, and then universal PCR was carried out to amplify the products and at the same time to add a sample-specific barcode to the product from each cell.

Example 4

Detection of Methylated Targets

A full-length mRNA for GAPDH has three target sequences GAPDH_1, GAPDH_2, and GAPDH_3, each target 50 bases in length. GAPDH_1 is upstream of a splice site, and has a position suspected of having an $m^1A$ modification at position 26, near a start codon. Pairs of detectors for each of the three target sequences are provided, where performing the assay as disclosed herein can generate countable amplicons corresponding to GAPDH_1, _2, and _3 respectively, indicating those target sequences are present in the mRNA sample. The count numbers may be adjusted quantitatively for minor count variations observed when detecting the three targets, when the GAPDH targets are known to be present in equimolar amounts. However, the detectors for GAPDH_1 generate no (or substantially fewer) countable amplicons when the $m^1A$ modification is present at position 26, compared to the expected counts with no modification at position 26. The detectors for GAPDH_2 and _3 can thus serve as positive controls for the presence of the full-length mRNA, regardless of $m^1A$ modification at position 26. Thus, the invention provides a method for detecting the presence of modifications, such as methylation, at positions of interest in the nucleic acids of a sample.

Example 5

Processing FFPE Tissues Using the Standard TempO-Seq™ FFPE Protocol and Performance Profiling of H&E-Stained FFPEs FFPE samples can be used in the standard TempO-Seq™ assay. In the FFPE preparation protocol, the FFPE was unstained, antibody stained, or H&E stained. A 1-2 mm² area of a 5 μm thick section of FFPE was sufficient, making TMAs, core biopsies, FNAs suitable for assay. The sample can be slide mounted or a curl.

Figure 5:
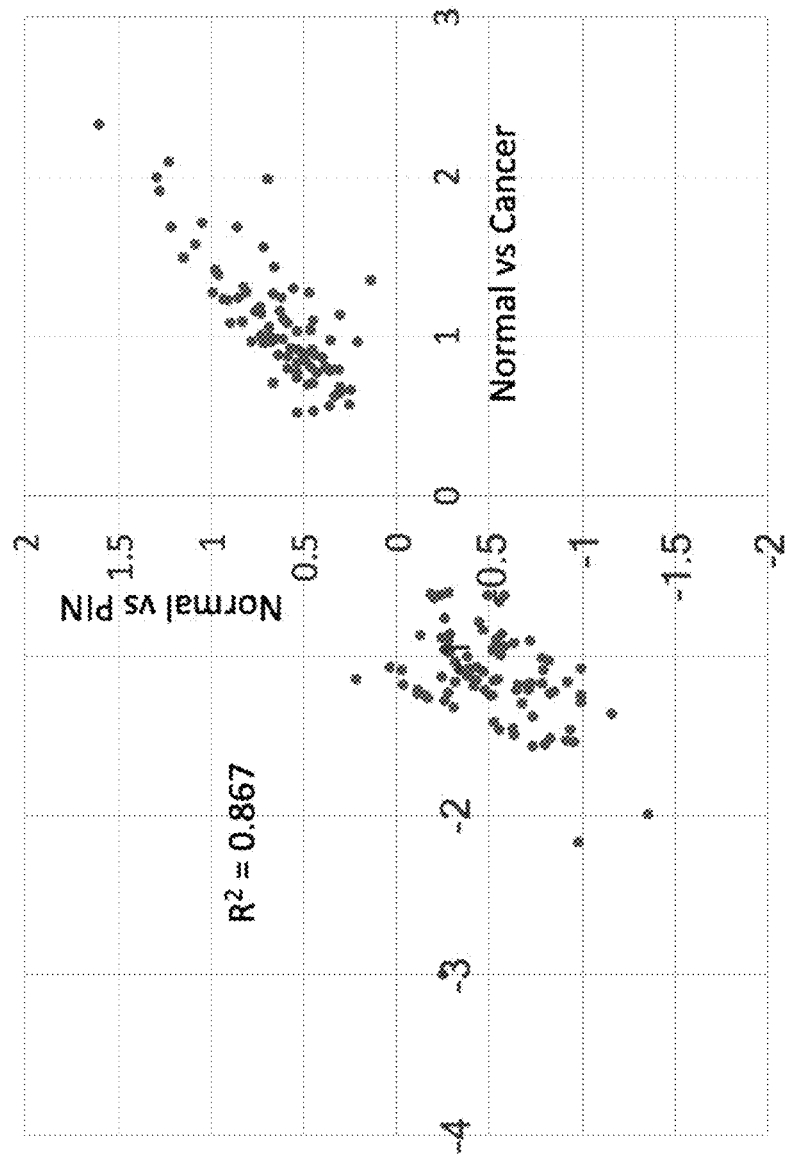
FIG. 5 compares expression between normal and PIN (prostatic intraepithelial neoplasia) versus normal and cancer, plotting for statistically significant genes, as discussed in Example 5.

FFPEs from five prostate cancer patients were H&E stained. Then 1 mm² areas were identified for prostate: normal, adjacent high grade prostatic intraepithelial neoplasia (PIN) or cancer epithelium. The areas were scraped and processed through the standard TempO-Seq™ assay for whole transcriptome. In FIG. 5, differential expression between normal and PIN versus normal and cancer was determined and plotted ($\log_2$-fold change) for statistically significant genes (adjusted p-value <0.05). Most genes that were differentially expressed in cancer were also differentially expressed in high grade PIN, indicating that at the molecular level, high grad PIN adjacent to cancer is in fact cancer in situ.

Example 6

Automated in Situ CellSensus™ Assay Process

The in situ TempO-Seq™ protocol was performed directly on slide-mounted FFPE tissue using an automated stainer (Bond RX, Leica BioSystems Inc., Buffalo Grove, Ill.). As illustrated in FIG. 6, the FFPE sample was deparaffinized and processed by the automated stainer through the point of detector oligo ligation. The automated stainer then stained the slides with antibodies (such as an anti-CD3 antibody) or optionally H&E (hematoxylin and eosin), performing (as desired) some of the staining steps manually, such as staining with eosine. The staining step includes immunostaining. The CellSensus™ imaging platform was used to perform pathological analysis and to image, and identify, select and/or mark areas for profiling.

The imager then automatically recovered probes from those areas and transferred them into PCR tubes that were processed through the remaining steps of the assay protocol described herein, including amplification, qPCR, and sequencing. The data was analyzed by TempO-SeqR™ software to generate a report. Any number of imaging platforms could have been used with appropriate hardware for elution, such as a capillary with fluidic control for applying the elution buffer to the surface of the sample.

Example 7

Single Cell Sensitivity

Figure 7:
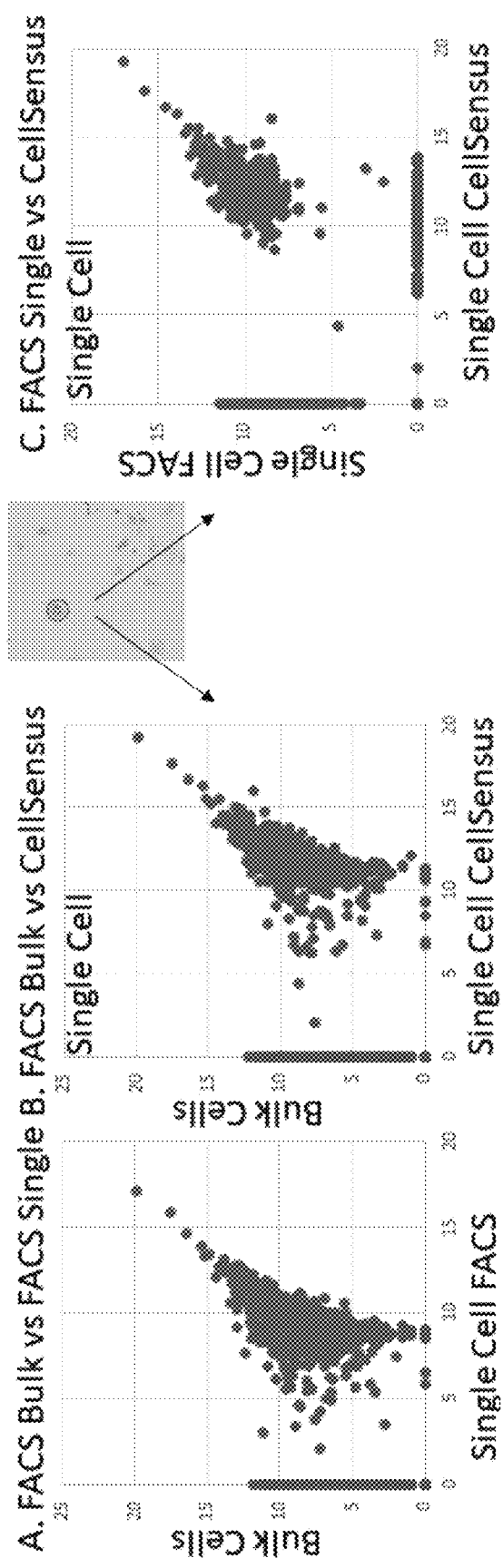
In FIG. 7, panel (A) shows the correlation of an assay of bulk 200 cells versus a single FACS-sorted cell. Panel (B) shows the correlation of the same 200-cell bulk and a single cell profiled using the CellSensus™ instrument. Panel (C) shows correlation of one single cell isolated by FACS versus a single cell isolated by the CellSensus™ instrument.

MCF-7 cells were processed through the in situ TempO-Seq™ Whole Transcriptome assay, then separated either by fluorescence-activated cell sorting (FACS) or Cytospin™ cytocentrifuge (Thermo Fisher Scientific, Waltham, Mass.). The Cytospin-separated cells were then picked by the CellSensus™ system. In FIG. 7, panel (A) shows correlation of an assay of bulk 200 cells versus a single FACS-sorted cell. Panel (B) shows the correlation of the same 200-cell bulk and a single cell profiled using the CellSensus™ instrument. Panel (C) shows correlation of one single cell isolated by FACS versus a single cell isolated by the CellSensus™ instrument. Stochastic gene expression was observed in single cells, with genes measured as expressed in bulk but not expressed in some of the individual single cells. Panel C shows genes that were expressed by one single cell but not another, and vice versa. Low-expressed genes were nevertheless measurable from single cells regardless of how they were picked, whether by FACS or by the CellSensus™ instrument.

Example 8

Focal Elution from FFPE Samples

Figure 8:
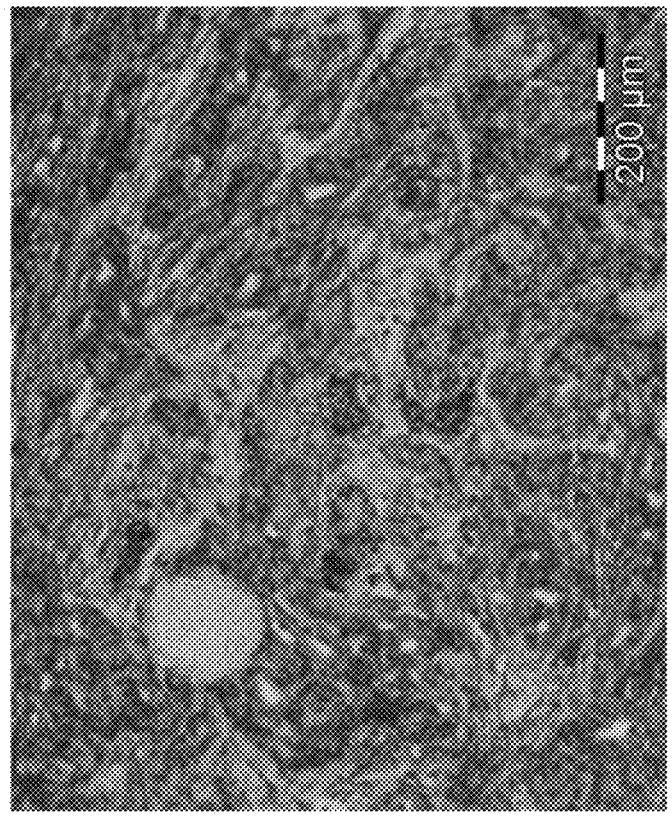
FIG. 8 shows images of a breast FFPE before and after automated elution by the CellSensus™ instrument, showing that a reagent in the eluent destains the exposed area, providing a positive record of the profiled area.
Figure 8:
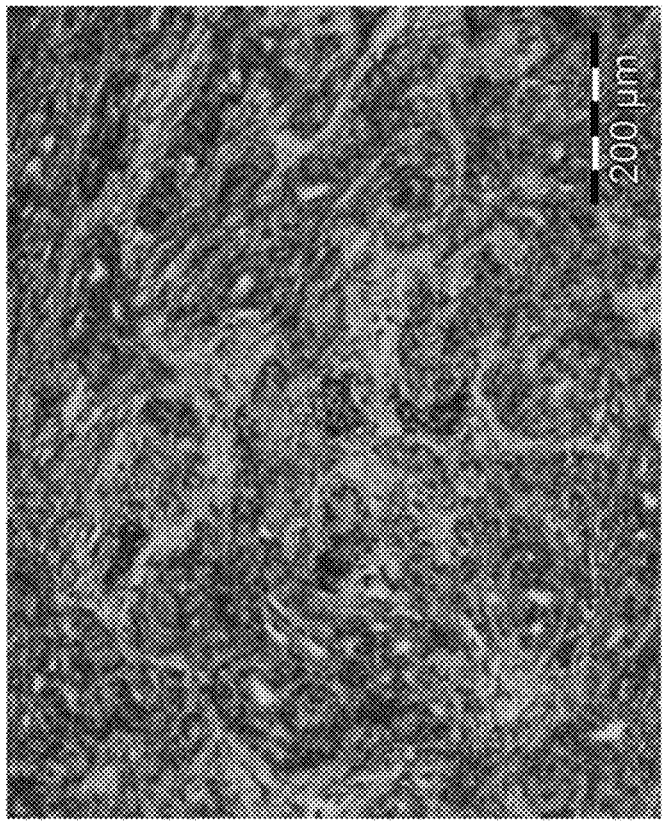

Breast FFPE was processed through the in situ assay on the Bond RX, then H&E stained. Areas of interest for profiling were digitally marked while performing IHC. The CellSensus™ instrument then carried out automated elution. A reagent in the eluent destained the exposed area, providing a positive record of the area profiled. This is evident from the pre-elution and post elution images in FIG. 8. The intensity of the blue staining was scanned in the pre- and post-elution images, clearly demonstrating the destaining and the ability of the CellSensus™ imager to assess and quantify the area from which the profiling data was obtained.

The CellSensus™ assay of H&E-stained breast cancer epithelium was compared to a 1 $mm^2$ area of scraped tissue (cancer and non-cancer), both after being processed on the Bond RX platform using the In Situ assay with a targeted breast cancer panel of 486 genes. Table 1 below compares the counts for genes with greater than 5000 counts (1st column), demonstrating that the assays correlate for some genes, but that the non-cancer tissue made a significant contribution, which the spatial resolution of the CellSensus™ assay addresses, reflected in the ratio (4th column) of CellSensus (2nd column) to scraped counts (3rd column).

TABLE 1

|  | CellSensus | Scraped | Ratio |
| --- | --- | --- | --- |
| MLPH | 47728 | 129773 | 0.4 |
| ESR1 | 20216 | 2740 | 7.4 |
| TGFB3 | 13275 | 2417 | 5.5 |
| RPLP0 | 12566 | 10820 | 1.2 |
| MDM4 | 11102 | 11494 | 1.0 |
| UCHL5 | 10990 | 2781 | 4.0 |
| PGR | 10980 | 4797 | 2.3 |
| YWHAB | 10626 | 1323 | 8.0 |
| SCUBE2 | 10131 | 1090 | 9.3 |
| TRFC | 10029 | 1716 | 5.8 |
| CDH1 | 9404 | 7482 | 1.3 |
| CDK4 | 8275 | 8623 | 1.0 |
| WNT5A | 8247 | 3591 | 2.3 |
| GRB7 | 7585 | 1207 | 6.3 |
| VEGFA | 7361 | 1192 | 6.2 |
| ERBB2 | 4403 | 3007 | 1.5 |

Example 9

Differentially Expressed Genes Between Cell Lines and Histologic Transitions A cell pellet mixture of MCF7 and Jurkat cells was fixed, embedded, and sectioned. Slides were processed through the in situ assay and then stained with an anti-CD3 antibody and hematoxylin. This staining was used to direct the selection of cells for gene expression profiling, for example a cluster of CD3 negative cells. Table 2 provides counts for the highest overexpressed genes in Jurkat (top set) and MCF7 (bottom set) for cell-type specific profiling directed by the antibody staining and IHC analysis.

TABLE 2

| gene name | MCF7 counts | Jurkat counts |
| --- | --- | --- |
| Jurkat set: | | |
| TSLP | 0 | 170 |
| GDF15 | 52 | 154 |
| SUPV3L1 | 2 | 183 |
| BLMH | 26 | 106 |
| ASAH1 | 0 | 145 |
| ICMT | 1 | 300 |
| RRS1 | 0 | 76 |
| FGR | 0 | 316 |
| PDHX | 0 | 119 |
| MCF7 set: | | |
| ESR1 | 305 | 1 |
| TFF1 | 392 | 2 |
| SLC6A14 | 166 | 2 |
| SPDEF | 104 | 0 |
| PPIC | 102 | 0 |

Figure 9:
FIG. 9 shows stained prostate FFPE tissue (left) and the same tissue after focal elution of a 130 μm diameter area by the CellSensus™ instrument (right). The destained area in the center demonstrated exquisite elution and collection from minute spatial areas. The precision of the collection areas is demonstrated in Example 9 and Table 3, where the individual areas of cancer tissue, normal epithelia tissue, and stroma, were distinguished by sharply different gene expression profiles.
Figure 9:

Profiling of 130 mm diameter areas of cancer and normal epithelium and stroma of prostate (Table 3) was carried out, as depicted FIG. 9, where the spatial resolution provided molecular specificity of biomarkers.

The ratio of detection between different cells, which can be spatially separated by imaging or histologically distinguished, can be 1:10, 1:100, 1:500, 1:1000, 1:2000, 1:5000 or greater. Where a marker is detected in a cancer cell and there is no (or negligible) detection in a normal or stromal cell, or vice versa, the methods of the invention can be said to provide absolute specificity.

TABLE 3

| biomarker | cancer | normal | stroma |
|---|---|---|---|
| MALAT1* | 768539 | 255266 | 110984 |
| DDX5* | 10190 | 13909 | 5560 |
| HNRNPA1* | 8272 | 319 | 0 |
| MT-ND6* | 6209 | 8050 | 5363 |
| EIF3E* | 4650 | 0 | 1256 |
| MLPH* | 4293 | 2 | 0 |
| RPS7* | 4037 | 0 | 0 |
| ELK4 | 3982 | 3728 | 0 |
| PTP4A1* | 3953 | 0 | 0 |
| MALT1* | 3480 | 0 | 0 |
| ABCC4† | 3317 | 0 | 0 |
| CDH1 | 3253 | 3349 | 0 |
| HPN* | 3227 | 0 | 0 |
| SPDEF* | 3135 | 0 | 0 |
| RNF167* | 3050 | 0 | 0 |
| TSC22D1 | 2905 | 0 | 0 |
| AKT2* | 2885 | 0 | 0 |
| CALR* | 2807 | 0 | 2 |
| KLK2‡ | 2793 | 0 | 0 |
| CAMP* | 2715 | 0 | 0 |
| FAM213A* | 2515 | 0 | 0 |
| RNF4* | 2463 | 0 | 0 |
| EBNA1BP2* | 2332 | 0 | 0 |
| APH1A* | 2238 | 0 | 0 |
| IER2* | 2216 | 0 | 0 |
| SUZ12* | 2179 | 0 | 0 |
| USO1* | 2086 | 0 | 0 |
| MAX* | 2052 | 0 | 0 |
| EPHB6* | 2043 | 0 | 0 |
| SAT1 | 0 | 3544 | 0 |
| SOCS4 | 0 | 3506 | 0 |
| NOP56 | 0 | 3130 | 0 |

Biomarkers with an asterisk (*) have previously been associated with prostate cancer.
ABCC4 (†), also known as MRP4, is a multidrug resistance gene associated with androgen signaling that pumps drugs out of cells.
KLK2 (‡) is the gene for Kallikrein 2, secreted by the prostate in cancer (together with PSA produced by KLK3), and is an important diagnostic marker.

The headings provided above are intended only to facilitate navigation within the document and should not be used to characterize the meaning of one portion of text compared to another. Skilled artisans will appreciate that additional embodiments are within the scope of the invention. The invention is defined only by the following claims; limitations from the specification or its examples should not be imported into the claims.

We claim:

1. A method for detecting a nucleic acid sequence from a selected area of a sample in situ, comprising in any order:
   imaging the sample for the presence or absence of an analyte;
   selecting an area of the sample less than 2 mm² based on the imaging;
   detecting a target nucleic acid sequence having a downstream region (DR) and an upstream region (UR), by
   (1) contacting at least the selected area of the sample with a downstream detector oligo (DDO) comprising a DR' portion that is complementary to the DR, and an upstream detector oligo (UDO) comprising a UR' portion that is complementary to the UR,
   (2) ligating the DR' and UR' if both are specifically hybridized to the DR and UR of a target sequence, and
   (3) eluting the ligation products from the selected area by addition of a basic elution fluid,
   whereby the ligation product indicates the presence of the target sequence in the selected area.

2. The method of claim 1, wherein the area is selected is a morphological feature.

3. The method of claim 1, wherein the sample is from an FFPE.

4. The method of claim 1, further comprising the step of deparaffinizing the sample.

5. The method of claim 1, further comprising the step of analyte retrieval.

6. The method of claim 5, wherein the analyte is an antigen or nucleic acid.

7. The method of claim 1, wherein the sample is imaged by histological stains.

8. The method of claim 1, wherein the sample is imaged by immunostaining.

9. The method of claim 1, wherein the sample is imaged with a histological stain and by immunostaining.

10. The method of claim 1, wherein the sample is dried after performing a step.

11. The method of claim 1, wherein a wash step is performed after detection steps (1) or (2).

12. The method of claim 1, wherein the selected area is less than 0.2, 0.02, or 0.002 mm².

13. The method of claim 1, wherein the target sequence is a portion of a cancer marker.

14. The method of claim 1, further comprising the step of reimaging the selected area, to verify collection of ligation products.

15. A method for detecting a neoplastic state of a cell by performing the method of claim 1 where a first cancer marker sequence is detected in the cell.

16. The method of claim 15, wherein the number of ligation products detected for a second cancer marker sequence is less than 10%, 1%, 0.01%, or 0.05% of the number of ligation products detected for the first cancer marker sequence.

17. The method of claim 16, wherein a cancer marker is detected a neoplastic cell and not detected in a normal cell, providing absolute specificity.

18. A method for generating a gene expression profile for a selected area, comprising performing the method of claim 1 for a plurality of target sequences.

19. A method for detecting a neoplastic state of a cells in a tissue by performing the method of claim 18 for a plurality cancer marker sequences on cells in two separate areas of the tissue.

20. A method for diagnosing a disease state by performing the method of claim 1, wherein the target sequence is detected in the area of a morphological feature.

21. A kit comprising the detector oligos of claim 1, a basic elution fluid, and a stain.

22. The method of claim 1, wherein elution step (3) comprises applying the basic elution fluid to the selected area of the sample in situ.

23. The method of claim 1, wherein elution step (3) comprises applying the basic elution fluid to the selected area of the sample using a capillary with fluidic control.

24. The method of claim 1, wherein elution step (3) comprises recovering the ligation products from the selected area of the sample in situ.

25. The method of claim 1, wherein elution step (3) comprises transferring the eluted ligation products using a capillary with fluidic control.

26. The method of claim 1, wherein elution step (3) comprises transferring the eluted ligation products to a container.

\* \* \* \* \*

UNITED STATES PATENT AND TRADEMARK OFFICE
CERTIFICATE OF CORRECTION

Page 1 of 1

PATENT NO. : 11,091,810 B2
APPLICATION NO. : 15/954546
DATED : August 17, 2021
INVENTOR(S) : Elliot Imler, Milos Babic and Bruce Seligmann It is certified that error appears in the above-identified patent and that said Letters Patent is hereby corrected as shown below:

In the Specification

Column 1, Line 36, the STATEMENT OF GOVERNMENT SUPPORT should read as follows:
STATEMENT OF GOVERNMENT SUPPORT
This invention was made with government support under grants R43 & R44 ES024107, R43 & R44 HG007339, R43 & R44 HG008917, R43 & R44 HG007815, awarded by the National Institutes of Health (NIH). The government has certain rights in the invention.

Signed and Sealed this
Second Day of September, 2025

Coke Morgan Stewart
*Acting Director of the United States Patent and Trademark Office*